US006417328B2

(12) United States Patent
Alnemri

(10) Patent No.: US 6,417,328 B2
(45) Date of Patent: *Jul. 9, 2002

(54) TRAIL RECEPTORS, NUCLEIC ACIDS ENCODING THE SAME, AND METHODS OF USE THEREOF

(75) Inventor: Emad S. Alnemri, Ambler, PA (US)

(73) Assignee: Thomas Jefferson Univeristy, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 65 days.

(21) Appl. No.: 09/134,618

(22) Filed: Aug. 14, 1998

Related U.S. Application Data

(60) Provisional application No. 60/055,906, filed on Aug. 15, 1997, now abandoned.

(51) Int. Cl.[7] ..................... C07K 14/715; C12N 15/12; C12N 5/10; C12N 15/63
(52) U.S. Cl. ..................... 530/350; 435/69.1; 435/71.1; 435/71.2; 435/471; 435/325; 435/320.1; 435/252.3; 435/254.11; 536/23.1; 536/23.5
(58) Field of Search .................... 530/350; 435/471, 435/69.1, 71.1, 71.2, 252.3, 254.11, 320.1, 325; 536/23.1, 23.5, 24.3, 24.31

(56) References Cited

FOREIGN PATENT DOCUMENTS

| EP | 867 509 A2 | 9/1998 |
| EP | 870 827 A2 | 10/1998 |
| WO | WO 98/30693 | 7/1998 |
| WO | WO 98/35986 | 8/1998 |

OTHER PUBLICATIONS

Suter et al., (1995), Gene vol. 163, pp. 263–266.*
Mikayama et al. Proc. Natl. Acad. Sci. USA vol. 90, pp. 10056–10060, 1993.*
Voet et al. Biochemistry. John Wiley & Sons, Inc., pp. 126–128 and 228–234, 1990.*
Chaudhary et al., "Death Receptor 5, a New Member of the TNFR Family, and DR4 Induce FADD–Dependent Apoptosis and Activate the FN–κB Pathway," *Immunity* 7:821–830, 1997.
Degli–Esposti et al., "Cloning and Characterization of TRAIL–R3, a Novel Member of the Emerging TRAIL Receptor Family," *J. Exp. Med.* 186(7):1165–1170, 1997.
MacFarlane et al., "Identification and Molecular Cloning of Two Novel Receptors for the Cytotoxic Ligand TRAIL," *The Journal Of Biological Chemistry* 272(41):25417–25420, 1997.
Pan et al., "an Antagonist Decoy Receptor and a Death Domain–Containing Receptor for TRAIL," *Science* 277:815–818, 1997.
Schneider et al., "Characterization of two receptors for TRAIL," *FEBS Letters* 416:329–334, 1997.
Screaton et al., "TRICK2, a new alternatively spliced receptor that transduces the cytotoxic signal from TRAIL," *Current Biology* 7:693–696, 1997.
Sheridan et al., "Control of TRAIL–Induced Apoptosis by a Family of Signaling and Decoy Receptors," *Science* 277:818–821, 1997.
Walczak et al., "TRAIL–R2: a novel apoptosis–mediating receptor for TRAIL," *The EMBO Journal* 16(17):5386–5397, 1997.
Wu et al., "KILLER/DR5 is a DNA damage–inducible p53–regulated death receptor gene," *Nature Genetics* 17:141–143, 1997.

* cited by examiner

*Primary Examiner*—Prema Mertz
(74) *Attorney, Agent, or Firm*—Seed Intellectual Property Law Group PLLC

(57) ABSTRACT

In accordance with the present invention, there are provided isolated mammalian TRAIL receptor proteins, antibodies thereto, therapeutic compositions, and nucleic acids encoding such. Bioassays and therapeutic methods employing invention DR5 and TRAIL-R3 proteins are also provided.

2 Claims, 9 Drawing Sheets

| | | |
|---|---|---|
| -51 | MEQRGQNAPAASGARKRHGPGPREARGARPGLRVPKTLVLVVAAVLLLVS | -2 |
| -1 | AESALITQQDLAPQQRVAPQQKRSSPSEGLCPPGHHISEDGRDCISCKYG | 49 |
| 50 | QDYSTHWNDLLFCLRCTRCDSGEVELSPCTTTRNTVCQCEEGTFREEDSP | 99 |
| 100 | EMCRKCRTGCPRGMVKVGDCTPWSDIECVHKESGIIIGVTVAAVVLIVAV | 149 |
| 150 | FVCKSLLWKKVLPYLKGICSGGGGDPERVDRSSQRPGAEDNVLNEIVSIL | 199 |
| 200 | QPTQVPEQEMEVQEPAEPTGVNMLSPGESEHLLEPAEAERSQRRRLLVPA | 249 |
| 250 | NEGDPTETLRQCFDDFADLVPFDSWEPLMRKLGLMDNEIKVAKAEAAGHR | 299 |
| 300 | DTLYTMLIKWVNKTGRDASVHTLLDALETLGERLAKQKIEDHLLSSGKFM | 349 |
| 350 | YLEGNADSAMS* | 360 |

Fig. 1A

| | | |
|---|---|---|
| -63 | MQGVKERFLPLGNSGDRAPRPPDGRGRVRPRTQDGVGNHTMARIPKTLKF | -14 |
| -13 | VVVIVAVLLPVLAYSATTARQEEVPQQTVAPQQQRHSFKGEECPAGSHRS | 37 |
| 38 | EHTGACNPCTEGVDYTNASNNEPSCFPCTVCKSDQKHKSSCTMTRDTVCQ | 87 |
| 88 | CKEGTFRNENSPEMCRKCSRCPSGEVQVSNCTSWDDIQCVEEFGANATVE | 137 |
| 138 | TPAAEETMNTSPGTPAPAAEETMNTSPGTPAAAEETMTTSPGTPAPAAE | 187 |
| 188 | ETMTTSPGTPAPAAEETMTTSPGTPASSHYLSCTIVGIIVLIVLLIVFV* | 236 |

Fig. 1B

| | | | |
|---|---|---|---|
| DR5 | 273 | SWEPLMRKLGLMDNEIK.VAKAEAAGHRDTLYTMLIKWVNKTG.RDASVH | 320 |
| DR4 | 356 | SWDQLMRQL LTKNEID.VVRAGTAGPGDALYAMLMKWVNKTG.RNASIH | 403 |
| DR3 | 346 | RWKEEVRTLGLREAEIEAVEVEIGR.FRDQQYEMLKRWRQQQP...AGLG | 391 |
| TNFR-1 | 330 | RWKEEVRRLGLSDHEIDRLELQNGRCLREAQYSMLATWRRRTPRREATLE | 379 |
| FAS | 228 | QVKGEVRKNGVNEAKIDEIKNDNVQDTAEQKVQLLRNWHQLHGKKEA.YD | 276 |
| CAR1 | 269 | EWKREGRALDLQENDLY.LAEQHDRVSCEPFYQMLNTWLNQQG.SKASVN | 313 |

| | | | |
|---|---|---|---|
| DR5 | 321 | TLLDALETLGERLAKQKIE | 339 |
| DR4 | 404 | TLLDALERMEERHAKEKIQ | 422 |
| DR3 | 392 | AVYAALKRMGLDGCVE LR | 410 |
| TNFR-1 | 380 | LLGRVLRDMDLLGCLEDIE | 398 |
| FAS | 277 | TLIKDLKKANLCTLAEKIQ | 239 |
| CAR1 | 314 | TLLETLPRIGLSGVADIIA | 333 |

*Fig. 1C*

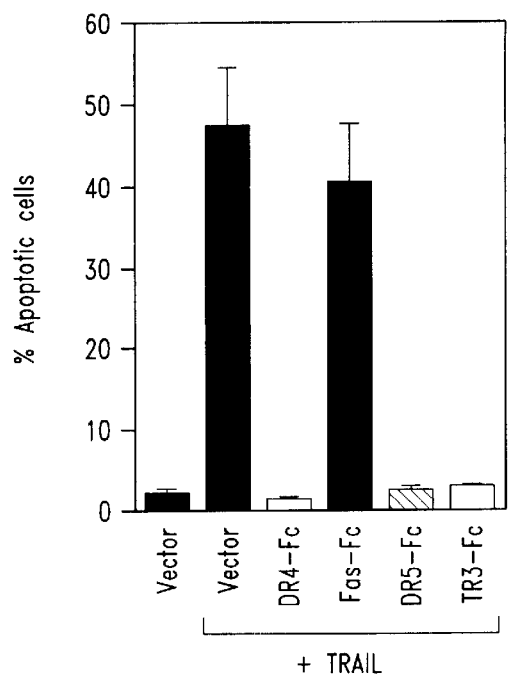
*Fig. 2B*
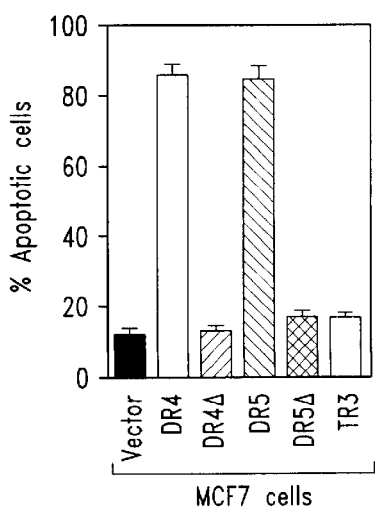 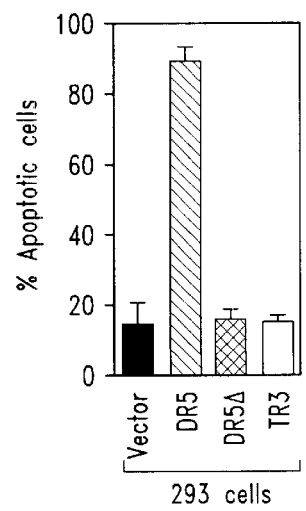 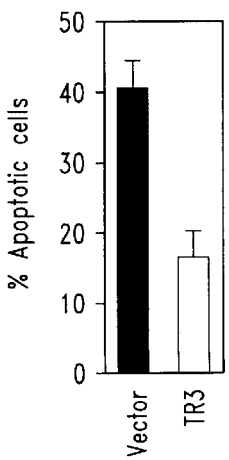
*Fig. 3A*    *Fig. 3B*    *Fig. 3C*

```
  1 ATGGAACAACGGGGACAGAACGCCCCGGCCGCTTCGGGGGCCCGGAAAAGGCACGGCCCA  60
  1 M  E  Q  R  G  Q  N  A  P  A  A  S  G  A  R  K  R  H  G  P   20

61 GGACCCAGGGAGGCGCGGGGAgCCAGGCCTGGGCTCCGGGTCCCCAAGACCCTTGTGCTC 120
 21 G  P  R  E  A  R  G  A  R  P  G  L  R  V  P  K  T  L  V  L   40

121 GTTGTCGCCGCGGTCCTGCTGTTGGTCTCAGCTGAGTCTGCTCTGATCACCCAACAAGAC 180
 41 V  V  A  A  V  L  L  L  V  S  A  E  S  A  L  I  T  Q  Q  D   60

181 CTAGCTCCCCAGCAGAGAGTGGCCCCACAACAAAAGAGGTCCAGCCCCTCAGAGGGATTG 240
 61 L  A  P  Q  Q  R  V  A  P  Q  Q  K  R  S  S  P  S  E  G  L   80

241 TGTCCACCTGGACACCATATCTCAGAAGACGGTAGAGATTGCATCTCCTGCAAATATGGA 300
 81 C  P  P  G  H  H  I  S  E  D  G  R  D  C  I  S  C  K  Y  G  100

301 CAGGACTATAGCACTCACTGGAATGACCTCCTTTTCTGCTTGCGCTGCACCAGGTGTGAT 360
101 Q  D  Y  S  T  H  W  N  D  L  L  F  C  L  R  C  T  R  C  D  120

361 TCAGGTGAAGTGGAGCTAAGTCCCTGCACCACGACCAGAAACACAGTGTGTCAGTGCGAA 420
121 S  G  E  V  E  L  S  P  C  T  T  T  R  N  T  V  C  Q  C  E  140

421 GAAGGCACCTTCCGGGAAGAAGATTCTCCTGAGATGTGCCGGAAGTGCCGCACAGGGTGT 480
141 E  G  T  F  R  E  E  D  S  P  E  M  C  R  K  C  R  T  G  C  160

481 CCCAGAGGGATGGTCAAGGTCGGTGATTGTACACCCTGGAGTGACATCGAATGTGTCCAC 540
161 P  R  G  M  V  K  V  G  D  C  T  P  W  S  D  I  E  C  V  H  180

541 AAAGAATCAGGTACAAAGCACAGTGGGGAAGCCCCAGCTGTGGAGGAGACGGTGACCTCC 600
181 K  E  S  G  T  K  H  S  G  E  A  P  A  V  E  E  T  V  T  S  200

601 AGCCCAGGGACTCCTGCCTCTCCCTGTTCTCTCtCAGGCATCATCATAGGAGTCACAGTT 660
201 S  P  G  T  P  A  S  P  C  S  L  S  G  I  I  I  G  V  T  V  220

661 GCAGCCGTAGTCTTGATTGTGGCTGTGTTTGTTTGCAAGTCTTTACTGTGGAAGAAAGTC 720
221 A  A  V  V  L  I  V  A  V  F  V  C  K  S  L  L  W  K  K  V  240
```

*Fig. 5A*

```
721  CTTCCTTACCTGAAAGGCATCTGCTCAGGTGGTGGTGGGGACCCTGAGCGTGTGGACAGA  780
241  L   P   Y   L   K   G   I   C   S   G   G   G   D   P   E   R   V   D   R       260

781  AGCTCACAACGACCTGGGGCTGAGGACAATGTCCTCAATGAGATCGTGAGTATCTTGCAG  840
261  S   S   Q   R   P   G   A   E   D   N   V   L   N   E   I   V   S   I   L   Q   280

841  CCCACCCAGGTCCCTGAGCAGGAAATGGAAGTCCAGGAGCCAGCAGAGCCAACAGGTGTC  900
281  P   T   Q   V   P   E   Q   E   M   E   V   Q   E   P   A   E   P   T   G   V   300

901  AACAAAACCgGGCgAgATGCCTCTGTCCACACCCTGCTGGATGCCTTGGAgACgCTGGGA  960
301  N   K   T   G   R   D   A   S   V   H   T   L   L   D   A   L   E   T   L   G   320

961  gAgAgACTTGCCAAGCAGAAGATTGAGGACCACTTGTTGAGCTCTGGAAAGTTCATGTAT  1020
321  E   R   L   A   K   Q   K   I   E   D   H   L   L   S   S   G   K   F   M   Y   340

1021 CTAGAAGGTAATGCAGACTCTGCCATGTCCTAA  1053
341  L   E   G   N   A   D   S   A   M   S   *       351
```

*Fig. 5B*

```
DR5s    1  MEQRGQNAPAASGARKRHGPGPREARGARPGLRVPKTLVLVVAAVLLLVS   50
           ||||||||||||||||||||||||||||||||||||||||||||||||||
DR5     1  MEQRGQNAPAASGARKRHGPGPREARGARPGLRVPKTLVLVVAAVLLLVS   50

51  AESALITQQDLAPQQRVAPQQKRSSPSEGLCPPGHHISEDGRDCISCKYG  100
           ||||||||||||||||||||||||||||||||||||||||||||||||||
       51  AESALITQQDLAPQQRVAPQQKRSSPSEGLCPPGHHISEDGRDCISCKYG  100

101  QDYSTHWNDLLFCLRCTRCDSGEVELSPCTTTRNTVCQCEEGTFREEDSP  150
           ||||||||||||||||||||||||||||||||||||||||||||||||||
      101  QDYSTHWNDLLFCLRCTRCDSGEVELSPCTTTRNTVCQCEEGTFREEDSP  150

151  EMCRKCRTGCPRGMVKVGDCTPWSDIECVHKESGTKHSGEAPAVEETVTS  200
           |||||||||||||||||||||||||||||||
      151  EMCRKCRTGCPRGMVKVGDCTPWSDIECVHKE..................  182

201  SPGTPASPCSLSGIIIGVTVAAVVLIVAVFVCKSLLWKKVLPYLKGICSG  250
                     ||||||||||||||||||||||||||||||||||||||||
      183  ..........SGIIIGVTVAAVVLIVAVFVCKSLLWKKVLPYLKGICSG  221

251  GGGDPERVDRSSQRPGAEDNVLNEIVSILQPTQVPEQEMEVQEPAEPTG.  299
           |||||||||||||||||||||||||||||||||||||||||||||||||
      222  GGGDPERVDRSSQRPGAEDNVLNEIVSILQPTQVPEQEMEVQEPAEPTGV  271

300  ...............................VNKTGRDASVH         310
                                          |||||||||||
      322  FDSWEPLMRKLGLMDNEIKVAKAEAAGHRDTLYTMLIKWVNKTGRDASVH  371

311  TLLDALETLGERLAKQKIEDHLLSSGKFMYLEGNADSAMS            350
           |||||||||||||||||||||||||||||||||||||||
      372  TLLDALETLGERLAKQKIEDHLLSSGKFMYLEGNADSAMS            411
```

Fig. 6

SEQUENCE LISTING

<160> NUMBER OF SEQ ID NOS: 6

<210> SEQ ID NO 1
<211> LENGTH: 1236
<212> TYPE: DNA
<213> ORGANISM: Homo sapiens
<220> FEATURE:
<221> NAME/KEY: CDS
<222> LOCATION: (1)..(1233)

<400> SEQUENCE: 1

```
atg gaa caa cgg gga cag aac gcc ccg gcc gct tcg ggg gcc cgg aaa    48
Met Glu Gln Arg Gly Gln Asn Ala Pro Ala Ala Ser Gly Ala Arg Lys
  1               5                  10                  15
agg cac ggc cca gga ccc agg gag gcg cgg gga gcc agg cct ggg ctc    96
Arg His Gly Pro Gly Pro Arg Glu Ala Arg Gly Ala Arg Pro Gly Leu
             20                  25                  30
cgg gtc ccc aag acc ctt gtg ctc gtt gtc gcc gcg gtc ctg ctg ttg   144
Arg Val Pro Lys Thr Leu Val Leu Val Val Ala Ala Val Leu Leu Leu
         35                  40                  45
gtc tca gct gag tct gct ctg atc acc caa caa gac cta gct ccc cag   192
Val Ser Ala Glu Ser Ala Leu Ile Thr Gln Gln Asp Leu Ala Pro Gln
     50                  55                  60
cag aga gtg gcc cca caa caa aag agg tcc agc ccc tca gag gga ttg   240
Gln Arg Val Ala Pro Gln Gln Lys Arg Ser Ser Pro Ser Glu Gly Leu
 65                  70                  75                  80
tgt cca cct gga cac cat atc tca gaa gac ggt aga gat tgc atc tcc   288
Cys Pro Pro Gly His His Ile Ser Glu Asp Gly Arg Asp Cys Ile Ser
                 85                  90                  95
tgc aaa tat gga cag gac tat agc act cac tgg aat gac ctc ctt ttc   336
Cys Lys Tyr Gly Gln Asp Tyr Ser Thr His Trp Asn Asp Leu Leu Phe
            100                 105                 110
tgc ttg cgc tgc acc agg tgt gat tca ggt gaa gtg gag cta agt ccc   384
Cys Leu Arg Cys Thr Arg Cys Asp Ser Gly Glu Val Glu Leu Ser Pro
        115                 120                 125
tgc acc acg acc aga aac aca gtg tgt cag tgc gaa gaa ggc acc ttc   432
Cys Thr Thr Thr Arg Asn Thr Val Cys Gln Cys Glu Glu Gly Thr Phe
    130                 135                 140
cgg gaa gaa gat tct cct gag atg tgc cgg aag tgc cgc aca ggg tgt   480
Arg Glu Glu Asp Ser Pro Glu Met Cys Arg Lys Cys Arg Thr Gly Cys
145                 150                 155                 160
ccc aga ggg atg gtc aag gtc ggt gat tgt aca ccc tgg agt gac atc   528
Pro Arg Gly Met Val Lys Val Gly Asp Cys Thr Pro Trp Ser Asp Ile
                165                 170                 175
gaa tgt gtc cac aaa gaa tca ggc atc atc ata gga gtc aca gtt gca   576
Glu Cys Val His Lys Glu Ser Gly Ile Ile Ile Gly Val Thr Val Ala
            180                 185                 190
gcc gta gtc ttg att gtg gct gtg ttt gtt tgc aag tct tta ctg tgg   624
Ala Val Val Leu Ile Val Ala Val Phe Val Cys Lys Ser Leu Leu Trp
        195                 200                 205
aag aaa gtc ctt cct tac ctg aaa ggc atc tgc tca ggt ggt ggt ggg   672
Lys Lys Val Leu Pro Tyr Leu Lys Gly Ile Cys Ser Gly Gly Gly Gly
    210                 215                 220
gac cct gag cgt gtg gac aga agc tca caa cga cct ggg gct gag gac   720
Asp Pro Glu Arg Val Asp Arg Ser Ser Gln Arg Pro Gly Ala Glu Asp
225                 230                 235                 240
aat gtc ctc aat gag atc gtg agt atc ttg cag ccc acc cag gtc cct   768
Asn Val Leu Asn Glu Ile Val Ser Ile Leu Gln Pro Thr Gln Val Pro
                245                 250                 255
gag cag gaa atg gaa gtc cag gag cca gca gag cca aca ggt gtc aac   816
Glu Gln Glu Met Glu Val Gln Glu Pro Ala Glu Pro Thr Gly Val Asn
            260                 265                 270
atg ttg tcc ccc ggg gag tca gag cat ctg ctg gaa ccg gca gaa gct   864
Met Leu Ser Pro Gly Glu Ser Glu His Leu Leu Glu Pro Ala Glu Ala
        275                 280                 285
gaa agg tct cag agg agg agg ctg gtt cca gca aat gaa ggt gat         912
Glu Arg Ser Gln Arg Arg Arg Leu Leu Val Pro Ala Asn Glu Gly Asp
    290                 295                 300
ccc act gag act ctg aga cag tgc ttc gat gac ttt gca gac ttg gtg   960
Pro Thr Glu Thr Leu Arg Gln Cys Phe Asp Asp Phe Ala Asp Leu Val
305                 310                 315                 320
ccc ttt gac tcc tgg gag ccg ctc atg agg aag ttg ggc ctc atg gac  1008
Pro Phe Asp Ser Trp Glu Pro Leu Met Arg Lys Leu Gly Leu Met Asp
                325                 330                 335
aat gag ata aag gtg gct aaa gct gag gca gcg ggc cac agg gac acc  1056
Asn Glu Ile Lys Val Ala Lys Ala Glu Ala Ala Gly His Arg Asp Thr
```

```
                Asn Glu Ile Lys Val Ala Lys Ala Glu Ala Ala Gly His Arg Asp Thr
                                340                 345                 350
    ttg tac acg atg ctg ata aag tgg gtc aac aaa acc ggg cga gat gcc         1104
    Leu Tyr Thr Met Leu Ile Lys Trp Val Asn Lys Thr Gly Arg Asp Ala
                    355                 360                 365
    tct gtc cac acc ctg ctg gat gcc ttg gag acg ctg gga gag aga ctt         1152
    Ser Val His Thr Leu Leu Asp Ala Leu Glu Thr Leu Gly Glu Arg Leu
                370                 375                 380
    gcc aag cag aag att gag gac cac ttg ttg agc tct gga aag ttc atg         1200
    Ala Lys Gln Lys Ile Glu Asp His Leu Leu Ser Ser Gly Lys Phe Met
    385                 390                 395                 400
    tat cta gaa ggt aat gca gac tct gcc atg tcc taa                         1236
    Tyr Leu Glu Gly Asn Ala Asp Ser Ala Met Ser
                        405                 410

<210> SEQ ID NO 2
<211> LENGTH: 411
<212> TYPE: PRT
<213> ORGANISM: Homo sapiens

<400> SEQUENCE: 2

Met Glu Gln Arg Gly Gln Asn Ala Pro Ala Ala Ser Gly Ala Arg Lys
    1               5                   10                  15
    Arg His Gly Pro Gly Pro Arg Glu Ala Arg Gly Ala Arg Pro Gly Leu
                    20                  25                  30
    Arg Val Pro Lys Thr Leu Val Leu Val Val Ala Ala Val Leu Leu Leu
                35                  40                  45
    Val Ser Ala Glu Ser Ala Leu Ile Thr Gln Gln Asp Leu Ala Pro Gln
            50                  55                  60
    Gln Arg Val Ala Pro Gln Gln Lys Arg Ser Ser Pro Ser Glu Gly Leu
    65                  70                  75                  80
    Cys Pro Pro Gly His His Ile Ser Glu Asp Gly Arg Asp Cys Ile Ser
                        85                  90                  95
    Cys Lys Tyr Gly Gln Asp Tyr Ser Thr His Trp Asn Asp Leu Leu Phe
                    100                 105                 110
    Cys Leu Arg Cys Thr Arg Cys Asp Ser Gly Glu Val Glu Leu Ser Pro
                115                 120                 125
    Cys Thr Thr Thr Arg Asn Thr Val Cys Gln Cys Glu Glu Gly Thr Phe
            130                 135                 140
    Arg Glu Glu Asp Ser Pro Glu Met Cys Arg Lys Cys Arg Thr Gly Cys
    145                 150                 155                 160
    Pro Arg Gly Met Val Lys Val Gly Asp Cys Thr Pro Trp Ser Asp Ile
                        165                 170                 175
    Glu Cys Val His Lys Glu Ser Gly Ile Ile Ile Gly Val Thr Val Ala
                    180                 185                 190
    Ala Val Val Leu Ile Val Ala Val Phe Val Cys Lys Ser Leu Leu Trp
                195                 200                 205
    Lys Lys Val Leu Pro Tyr Leu Lys Gly Ile Cys Ser Gly Gly Gly Gly
            210                 215                 220
    Asp Pro Glu Arg Val Asp Arg Ser Ser Gln Arg Pro Gly Ala Glu Asp
    225                 230                 235                 240
    Asn Val Leu Asn Glu Ile Val Ser Ile Leu Gln Pro Thr Gln Val Pro
                        245                 250                 255
    Glu Gln Glu Met Glu Val Gln Glu Pro Ala Glu Pro Thr Gly Val Asn
                    260                 265                 270
    Met Leu Ser Pro Gly Glu Ser Glu His Leu Leu Glu Pro Ala Glu Ala
                275                 280                 285
    Glu Arg Ser Gln Arg Arg Arg Leu Leu Val Pro Ala Asn Glu Gly Asp
            290                 295                 300
    Pro Thr Glu Thr Leu Arg Gln Cys Phe Asp Asp Phe Ala Asp Leu Val
    305                 310                 315                 320
    Pro Phe Asp Ser Trp Glu Pro Leu Met Arg Lys Leu Gly Leu Met Asp
                        325                 330                 335
    Asn Glu Ile Lys Val Ala Lys Ala Glu Ala Ala Gly His Arg Asp Thr
                    340                 345                 350
    Leu Tyr Thr Met Leu Ile Lys Trp Val Asn Lys Thr Gly Arg Asp Ala
                355                 360                 365
    Ser Val His Thr Leu Leu Asp Ala Leu Glu Thr Leu Gly Glu Arg Leu
            370                 375                 380
    Ala Lys Gln Lys Ile Glu Asp His Leu Leu Ser Ser Gly Lys Phe Met
    385                 390                 395                 400
    Tyr Leu Glu Gly Asn Ala Asp Ser Ala Met Ser
                        405                 410

<210> SEQ ID NO 3
<211> LENGTH: 900
```

```
<212> TYPE: DNA
<213> ORGANISM: Homo sapiens
<220> FEATURE:
<221> NAME/KEY: CDS
<222> LOCATION: (1)..(897)

<400> SEQUENCE: 3 atg caa ggg gtg aag gag cgc ttc cta ccg tta ggg aac tct ggg gac      48
    Met Gln Gly Val Lys Glu Arg Phe Leu Pro Leu Gly Asn Ser Gly Asp
    1               5                   10                  15
    aga gcg ccc cgg ccg cct gat ggc cga ggc agg gtg cga ccc agg acc      96
    Arg Ala Pro Arg Pro Pro Asp Gly Arg Gly Arg Val Arg Pro Arg Thr
                20                  25                  30
    caa gac ggc gtc ggg aac cat acc atg gcc cgg atc ccc aag acc cta     144
    Gln Asp Gly Val Gly Asn His Thr Met Ala Arg Ile Pro Lys Thr Leu
            35                  40                  45
    aag ttc gtc gtc gtc atc gtc gcg gtc ctg ctg cca gtc cta gct tac     192
    Lys Phe Val Val Val Ile Val Ala Val Leu Leu Pro Val Leu Ala Tyr
        50                  55                  60
    tct gcc acc act gcc cgg cag gag gaa gtt ccc cag cag aca gtg gcc     240
    Ser Ala Thr Thr Ala Arg Gln Glu Glu Val Pro Gln Gln Thr Val Ala
    65                  70                  75                  80
    cca cag caa cag agg cac agc ttc aag ggg gag tgt cca gca gga         288
    Pro Gln Gln Gln Arg His Ser Phe Lys Gly Glu Glu Cys Pro Ala Gly
                    85                  90                  95
    tct cat aga tca gaa cat act gga gcc tgt aac ccg tgc aca gag ggt     336
    Ser His Arg Ser Glu His Thr Gly Ala Cys Asn Pro Cys Thr Glu Gly
                100                 105                 110
    gtg gat tac acc aac gct tcc aac aat gaa cct tct tgc ttc cca tgt     384
    Val Asp Tyr Thr Asn Ala Ser Asn Asn Glu Pro Ser Cys Phe Pro Cys
            115                 120                 125
    aca gtt tgt aaa tca gat caa aaa cat aaa agt tcc tgc acc atg acc     432
    Thr Val Cys Lys Ser Asp Gln Lys His Lys Ser Ser Cys Thr Met Thr
        130                 135                 140
    aga gac aca gtg tgt cag tgt aaa gaa ggc acc ttc cgg aat gaa aac     480
    Arg Asp Thr Val Cys Gln Cys Lys Glu Gly Thr Phe Arg Asn Glu Asn
    145                 150                 155                 160
    tcc cca gag atg tgc cgg aag tgt agc agg tgc cct agt ggg gaa gtc     528
    Ser Pro Glu Met Cys Arg Lys Cys Ser Arg Cys Pro Ser Gly Glu Val
                    165                 170                 175
    caa gtc agt aat tgt acg tcc tgg gat gat atc cag tgt gtt gaa gaa     576
    Gln Val Ser Asn Cys Thr Ser Trp Asp Asp Ile Gln Cys Val Glu Glu
                180                 185                 190
    ttt ggt gcc aat gcc act gtg gaa acc cca gct gct gaa gag aca atg     624
    Phe Gly Ala Asn Ala Thr Val Glu Thr Pro Ala Ala Glu Glu Thr Met
            195                 200                 205
    aac acc agc ccg ggg act cct gcc cca gct gct gaa gag aca atg aac     672
    Asn Thr Ser Pro Gly Thr Pro Ala Pro Ala Ala Glu Glu Thr Met Asn
        210                 215                 220
    acc agc cca ggg act cct gcc cca gct gct gaa gag aca atg acc acc     720
    Thr Ser Pro Gly Thr Pro Ala Pro Ala Ala Glu Glu Thr Met Thr Thr
    225                 230                 235                 240
    agc ccg ggg act cct gcc cca gct gct gaa gag aca atg acc acc agc     768
    Ser Pro Gly Thr Pro Ala Pro Ala Ala Glu Glu Thr Met Thr Thr Ser
                    245                 250                 255
    ccg ggg act cct gcc cca gct gct gaa gag aca atg acc acc agc ccg     816
    Pro Gly Thr Pro Ala Pro Ala Ala Glu Glu Thr Met Thr Thr Ser Pro
                260                 265                 270
    ggg act cct gcc tct tct cat tac ctc tca tgc acc atc gta ggg atc     864
    Gly Thr Pro Ala Ser Ser His Tyr Leu Ser Cys Thr Ile Val Gly Ile
            275                 280                 285
    ata gtt cta att gtg ctt ctg att gtg ttt gtt tga                     900
    Ile Val Leu Ile Val Leu Leu Ile Val Phe Val
        290                 295

<210> SEQ ID NO 4
<211> LENGTH: 299
<212> TYPE: PRT
<213> ORGANISM: Homo sapiens

<400> SEQUENCE: 4

Met Gln Gly Val Lys Glu Arg Phe Leu Pro Leu Gly Asn Ser Gly Asp
    1               5                   10                  15
    Arg Ala Pro Arg Pro Pro Asp Gly Arg Gly Arg Val Arg Pro Arg Thr
                20                  25                  30
    Gln Asp Gly Val Gly Asn His Thr Met Ala Arg Ile Pro Lys Thr Leu
```

-continued

```
                    35                  40                  45
        Lys Phe Val Val Ile Val Ala Val Leu Leu Pro Val Leu Ala Tyr
         50                  55                  60
        Ser Ala Thr Thr Ala Arg Gln Glu Val Pro Gln Gln Thr Val Ala
         65                  70                  75                  80
        Pro Gln Gln Arg His Ser Phe Lys Gly Glu Cys Pro Ala Gly
                         85                  90                  95
        Ser His Arg Ser Glu His Thr Gly Ala Cys Asn Pro Cys Thr Glu Gly
                    100                 105                 110
        Val Asp Tyr Thr Asn Ala Ser Asn Asn Glu Pro Ser Cys Phe Pro Cys
                    115                 120                 125
        Thr Val Cys Lys Ser Asp Gln Lys His Lys Ser Ser Cys Thr Met Thr
                    130                 135                 140
        Arg Asp Thr Val Cys Gln Cys Lys Glu Gly Thr Phe Arg Asn Glu Asn
        145                 150                 155                 160
        Ser Pro Glu Met Cys Arg Lys Cys Ser Arg Cys Pro Ser Gly Glu Val
                         165                 170                 175
        Gln Val Ser Asn Cys Thr Ser Trp Asp Asp Ile Gln Cys Val Glu Glu
                    180                 185                 190
        Phe Gly Ala Asn Ala Thr Val Glu Thr Pro Ala Ala Glu Glu Thr Met
                    195                 200                 205
        Asn Thr Ser Pro Gly Thr Pro Ala Pro Ala Ala Glu Glu Thr Met Asn
                    210                 215                 220
        Thr Ser Pro Gly Thr Pro Ala Pro Ala Ala Glu Glu Thr Met Thr Thr
        225                 230                 235                 240
        Ser Pro Gly Thr Pro Ala Pro Ala Ala Glu Glu Thr Met Thr Thr Ser
                         245                 250                 255
        Pro Gly Thr Pro Ala Pro Ala Ala Glu Glu Thr Met Thr Thr Ser Pro
                    260                 265                 270
        Gly Thr Pro Ala Ser Ser His Tyr Leu Ser Cys Thr Ile Val Gly Ile
                    275                 280                 285
        Ile Val Leu Ile Val Leu Leu Ile Val Phe Val
        290                 295
```

<210> SEQ ID NO 5
<211> LENGTH: 1053
<212> TYPE: DNA
<213> ORGANISM: Homo sapiens
<220> FEATURE:
<221> NAME/KEY: CDS
<222> LOCATION: (1)..(1050)

<400> SEQUENCE: 5

```
atg gaa caa cgg gga cag aac gcc ccg gcc gct tcg ggg gcc cgg aaa      48
Met Glu Gln Arg Gly Gln Asn Ala Pro Ala Ala Ser Gly Ala Arg Lys
  1               5                  10                  15
agg cac ggc cca gga ccc agg gag gcg cgg gga gcc agg cct ggg ctc      96
Arg His Gly Pro Gly Pro Arg Glu Ala Arg Gly Ala Arg Pro Gly Leu
                 20                  25                  30
cgg gtc ccc aag acc ctt gtg ctc gtt gtc gcc gcg gtc ctg ctg ttg     144
Arg Val Pro Lys Thr Leu Val Leu Val Val Ala Ala Val Leu Leu Leu
             35                  40                  45
gtc tca gct gag tct gct ctg atc acc caa caa gac cta gct ccc cag     192
Val Ser Ala Glu Ser Ala Leu Ile Thr Gln Gln Asp Leu Ala Pro Gln
 50                  55                  60
cag aga gtg gcc cca caa caa aag agg tcc agc ccc tca gag gga ttg     240
Gln Arg Val Ala Pro Gln Gln Lys Arg Ser Ser Pro Ser Glu Gly Leu
 65                  70                  75                  80
tgt cca cct gga cac cat atc tca gaa gac ggt aga gat tgc atc tcc     288
Cys Pro Pro Gly His His Ile Ser Glu Asp Gly Arg Asp Cys Ile Ser
                 85                  90                  95
tgc aaa tat gga cag gac tat agc act cac tgg aat gac ctc ctt ttc     336
Cys Lys Tyr Gly Gln Asp Tyr Ser Thr His Trp Asn Asp Leu Leu Phe
            100                 105                 110
tgc ttg cgc tgc acc agg tgt gat tca ggt gaa gtg gag cta agt ccc     384
Cys Leu Arg Cys Thr Arg Cys Asp Ser Gly Glu Val Glu Leu Ser Pro
            115                 120                 125
tgc acc acg acc aga aac aca gtg tgt cag tgc gaa gaa ggc acc ttc     432
Cys Thr Thr Thr Arg Asn Thr Val Cys Gln Cys Glu Glu Gly Thr Phe
        130                 135                 140
cgg gaa gaa gat tct cct gag atg tgc cgg aag tgc cgc aca ggg tgt     480
Arg Glu Glu Asp Ser Pro Glu Met Cys Arg Lys Cys Arg Thr Gly Cys
145                 150                 155                 160
ccc aga ggg atg gtc aag gtc ggt gat tgt aca ccc tgg agt gac atc     528
Pro Arg Gly Met Val Lys Val Gly Asp Cys Thr Pro Trp Ser Asp Ile
                165                 170                 175
gaa tgt gtc cac aaa gaa tca ggt aca aag cac agt ggg gaa gcc cca     576
```

```
    Glu Cys Val His Lys Glu Ser Gly Thr Lys His Ser Gly Glu Ala Pro
                    180                 185                 190
    gct gtg gag gag acg gtg acc tcc agc cca ggg act cct gcc tct ccc     624
    Ala Val Glu Glu Thr Val Thr Ser Ser Pro Gly Thr Pro Ala Ser Pro
                195                 200                 205
    tgt tct ctc tca ggc atc ata gga gtc aca gtt gca gcc gta gtc         672
    Cys Ser Leu Ser Gly Ile Ile Gly Val Thr Val Ala Ala Val Val
            210                 215                 220
    ttg att gtg gct gtg ttt gtt tgc aag tct tta ctg tgg aag aaa gtc     720
    Leu Ile Val Ala Val Phe Val Cys Lys Ser Leu Leu Trp Lys Lys Val
    225                 230                 235                 240
    ctt cct tac ctg aaa ggc atc tgc tca ggt ggt ggt ggg gac cct gag     768
    Leu Pro Tyr Leu Lys Gly Ile Cys Ser Gly Gly Gly Gly Asp Pro Glu
                245                 250                 255
    cgt gtg gac aga agc tca caa cga cct ggg gct gag gac aat gtc ctc     816
    Arg Val Asp Arg Ser Ser Gln Arg Pro Gly Ala Glu Asp Asn Val Leu
                260                 265                 270
    aat gag atc gtg agt atc ttg cag ccc acc cag gtc cct gag cag gaa     864
    Asn Glu Ile Val Ser Ile Leu Gln Pro Thr Gln Val Pro Glu Gln Glu
                275                 280                 285
    atg gaa gtc cag gag cca gca gag cca aca ggt gtc aac aaa acc ggg     912
    Met Glu Val Gln Glu Pro Ala Glu Pro Thr Gly Val Asn Lys Thr Gly
                290                 295                 300
    cga gat gcc tct gtc cac acc ctg ctg gat gcc ttg gag acg ctg gga     960
    Arg Asp Ala Ser Val His Thr Leu Leu Asp Ala Leu Glu Thr Leu Gly
    305                 310                 315                 320
    gag aga ctt gcc aag cag aag att gag gac cac ttg ttg agc tct gga    1008
    Glu Arg Leu Ala Lys Gln Lys Ile Glu Asp His Leu Leu Ser Ser Gly
                325                 330                 335
    aag ttc atg tat cta gaa ggt aat gca gac tct gcc atg tcc taa        1053
    Lys Phe Met Tyr Leu Glu Gly Asn Ala Asp Ser Ala Met Ser
                340                 345                 350

<210> SEQ ID NO 6
<211> LENGTH: 350
<212> TYPE: PRT
<213> ORGANISM: Homo sapiens

<400> SEQUENCE: 6

Met Glu Gln Arg Gly Gln Asn Ala Pro Ala Ala Ser Gly Ala Arg Lys
    1               5                   10                  15
    Arg His Gly Pro Gly Pro Arg Glu Ala Arg Gly Ala Arg Pro Gly Leu
                    20                  25                  30
    Arg Val Pro Lys Thr Leu Val Leu Val Val Ala Ala Val Leu Leu Leu
                35                  40                  45
    Val Ser Ala Glu Ser Ala Leu Ile Thr Gln Gln Asp Leu Ala Pro Gln
        50                  55                  60
    Gln Arg Val Ala Pro Gln Gln Lys Arg Ser Ser Pro Ser Glu Gly Leu
    65                  70                  75                  80
    Cys Pro Pro Gly His His Ile Ser Glu Asp Gly Arg Asp Cys Ile Ser
                    85                  90                  95
    Cys Lys Tyr Gly Gln Asp Tyr Ser Thr His Trp Asn Asp Leu Leu Phe
                    100                 105                 110
    Cys Leu Arg Cys Thr Arg Cys Asp Ser Gly Glu Val Glu Leu Ser Pro
                115                 120                 125
    Cys Thr Thr Thr Arg Asn Thr Val Cys Gln Cys Glu Glu Gly Thr Phe
            130                 135                 140
    Arg Glu Glu Asp Ser Pro Glu Met Cys Arg Lys Cys Arg Thr Gly Cys
    145                 150                 155                 160
    Pro Arg Gly Met Val Lys Val Gly Asp Cys Thr Pro Trp Ser Asp Ile
                    165                 170                 175
    Glu Cys Val His Lys Glu Ser Gly Thr Lys His Ser Gly Glu Ala Pro
                    180                 185                 190
    Ala Val Glu Glu Thr Val Thr Ser Ser Pro Gly Thr Pro Ala Ser Pro
                195                 200                 205
    Cys Ser Leu Ser Gly Ile Ile Gly Val Thr Val Ala Ala Val Val
            210                 215                 220
    Leu Ile Val Ala Val Phe Val Cys Lys Ser Leu Leu Trp Lys Lys Val
    225                 230                 235                 240
    Leu Pro Tyr Leu Lys Gly Ile Cys Ser Gly Gly Gly Gly Asp Pro Glu
                245                 250                 255
    Arg Val Asp Arg Ser Ser Gln Arg Pro Gly Ala Glu Asp Asn Val Leu
                260                 265                 270
    Asn Glu Ile Val Ser Ile Leu Gln Pro Thr Gln Val Pro Glu Gln Glu
                275                 280                 285
    Met Glu Val Gln Glu Pro Ala Glu Pro Thr Gly Val Asn Lys Thr Gly
                290                 295                 300
```

-continued

```
Arg Asp Ala Ser Val His Thr Leu Leu Asp Ala Leu Glu Thr Leu Gly
305                 310                 315                 320
Glu Arg Leu Ala Lys Gln Lys Ile Glu Asp His Leu Leu Ser Ser Gly
            325                 330                 335
Lys Phe Met Tyr Leu Glu Gly Asn Ala Asp Ser Ala Met Ser
            340                 345                 350
```

TRAIL RECEPTORS, NUCLEIC ACIDS ENCODING THE SAME, AND METHODS OF USE THEREOF

CROSS-REFERENCE TO RELATED APPLICATION

This application claims priority from United States provisional application Ser. No. 60/055,906, filed Aug. 15, 1997, now abandoned.

STATEMENT OF GOVERNMENT INTEREST

This invention was made with government support under grant number AG 13487 awarded by the National Institutes of Health. The government has certain rights in the invention.

BACKGROUND INFORMATION

Apoptosis is a normal physiological process of cell death that plays a critical role in the regulation of tissue homeostasis by ensuring that the rate of new cell accumulation produced by cell division is offset by a commensurate rate of cell loss due to death. It has now become clear that disturbances in apoptosis, also referred to as physiological cell death or programmed cell death, that prevent or delay normal cell turnover can be just as important to the pathogenesis of diseases as are known abnormalities in the regulation of proliferation and the cell cycle. Like cell division, which is controlled through complex interactions between cell cycle regulatory proteins, apoptosis is similarly regulated under normal circumstances by the interaction of gene products that either induce or inhibit cell death.

The stimuli which regulate the function of these apoptotic gene products include both extracellular and intracellular signals. Either the presence or the removal of a particular stimuli can be sufficient to evoke a positive or negative apoptotic signal. For example, physiological stimuli that prevent or inhibit apoptosis include, for example, growth factors, extracellular matrix, CD40 ligand, viral gene products, neutral amino acids, zinc, estrogen, and androgens. In contrast, stimuli which promote apoptosis include growth factors such as tumor necrosis factor (TNF), Fas, and transforming growth factor β (TGFβ), neurotransmitters, growth factor withdrawal, loss of extracellular matrix attachment, intracellular calcium and glucocorticoids, for example.

Some of the well known regulators of apoptosis are cytokines of the tumor necrosis factor (TNF) ligand family, such as Fas ligand (Fas L) and TNF, which induce apoptosis by activation of their corresponding receptors, Fas and TNFR-1 (Nagata, S. (1997) *Cell* 88, 355-36S). These two receptors belong to a rapidly expanding family (collectively known as the TNF-receptor family) containing at least eleven known members (Nagata, S. (1997) *Cell* 88, 355-365; Chinnaiyan, A. M. et al. (1997) Σχλευχε 6, 111-113). Members of this family contain an extracellular ligand-binding domain, of 2-6 cysteine-rich repeats, which is about 25% conserved between different family members. The cytoplasmic region is less conserved between various members except for a stretch of about 80 amino acids present in Fas, TNFR-1, DR3/Wsl-1/Apo-3/TRAMP, CAR-1 and DR4 (Nagata, S. (1997) *Cell* 88, 355-365; and references therein). This intracellular region which has been designated the cytoplasmic "death domain" is responsible for transducing the death signal.

Activation of Fas results in recruitment of the Fas-associated death domain-containing molecule FADD/MORT-1, to the receptor complex (Boldin M. P. et al. (1995) *J. Biol. Chem.* 270, 7795–7798; Chinnaiyan A. M. et al. (1995) *Cell* 81, 505–512; Kischkel F. C. (1995) *EMBO J.* 14, 5579–5588). The resulting signaling complex then triggers activation of the caspase apoptotic pathway through interaction of the N-terminal death effector domain (DED) of FADD with the corresponding motifs in the prodomain of caspase-8 (Mch5/MACH/FLICE) and probably caspase-10 (Mch4) (Boldin M. P. et al. (1996) *Cell* 85, 803–815; Bretz J. D. et al. (1996) *Cell* 85, 817–827; Alnemri E. S. et al. (1996) *Proc. Natl. Sci. USA.* 93, 7464–7469; Alnemri E. S. et al. (1996) *Cell* 87, 171.

In contrast to Fas, activation of TNFR-1 or DR3 results in recruitment of another death domain-containing adaptor molecule known as TRAD (Chinnaiyan A. M. et al. (1996) *Science* 274, 990–991; Goeddel D. V. et al. (1995) *Cell* 81: 495–504). TRADD, can associate with a number of signaling molecules, including FADD, TRAF2, and RIP and as a result can transduce an apoptotic signal as well as activate NF-kB (Goeddel D. V. et al. (1996) *Cell* 84, 299–308; Baichwal V. et al. (1996) *Immunity* 4, 387–396). Consequently, engagement of TNFR-1 or DR3 can signal an array of diverse biological activities.

Recently, a new member of the TNF family known as TRAIL or Apo-2 ligand was identified and shown to induce apoptosis in a variety of tumor cell lines (Davis T. D. et al. (1995) *Immunity* 3 673–682: Ashkenazi A. et al. (1996) *J. Biol. Chem.* 271, 12687–12690; Ashkenazi A. et al. (1996) *Curr. Biol.* 6, 750–752). However, it is unclear what physiological control mechanisms regulate this form of programmed cell death or how the cell death pathways interact with other physiological processes within the organism.

Apoptosis functions in maintaining tissue homeostasis in a range of physiological processes such as embryonic development, immune cell regulation and normal cellular turnover. Therefore, the dysfunction, or loss of regulated apoptosis can lead to a variety of pathological disease states. For example, the loss of apoptosis can lead to the pathological accumulation of self-reactive lymphocytes such as that occurring with many autoimmune diseases. Inappropriate loss of apoptosis can also lead to the accumulation of virally infected cells and of hyperproliferative cells such an neoplastic or tumor cells. Similarly, the inappropriate activation of apoptosis can also contribute to a variety of pathological disease states including, for example, acquired immunodeficiency syndrome (AIDS), neurodegenerative diseases and ischemic injury. Treatments which are specifically designed to modulate the apoptotic pathways in these and other pathological conditions can change the natural progression of many of these diseases.

Thus, there exists a need to identify new apoptotic genes and their gene products and for methods of modulating this process for the therapeutic treatment of human diseases. The present invention satisfies this need and provides related advantages as well.

SUMMARY OF THE INVENTION

In accordance with the present invention, there are provided novel isolated mammalian members of the TRAIL-receptor family, designated DR5, TRAIL-R3, and splice variants thereof including DR5s. These invention proteins, or fragments thereof, are useful as immunogens for producing anti-DR5 or anti-TRAIL-R3 antibodies, or in therapeutic compositions containing such proteins and/or antibodies. The DR5 and TRAIL-R3 proteins are also useful in bioassays to identify agonists and antagonists thereto.

In accordance with the present invention, there are also provided isolated nucleic acids encoding novel DR5 or TRAIL-R3 proteins. Further provided are vectors containing invention nucleic acids, probes that hybridize thereto, host cells transformed therewith, antisense oligonucleotides thereto and related compositions. The nucleic acid molecules described herein can be incorporated into a variety of recombinant expression systems known to those of skill in the art to readily produce isolated recombinant DR5 or TRAIL-R3 proteins. In addition, the nucleic acid molecules of the present invention are useful as probes for assaying for the presence and/or amount of a DR5 or TRAIL-R3 gene or mRNA transcript in a given sample. The nucleic acid molecules described herein, and oligonucleotide fragments thereof, are also useful as primers and/or templates in a PCR reaction for amplifying nucleic acids encoding DR5 or TRAIL-R3 proteins. Also provided are transgenic non-human mammals that express the invention proteins.

Antibodies that are immunoreactive with invention DR5 or TRAIL-R3 proteins are also provided. These antibodies are useful in diagnostic assays to determine levels of DR5 or TRAIL-R3 proteins present in a given sample, e.g., tissue samples, Western blots, and the like. The antibodies can also be used to purify DR5 or TRAIL-R3 proteins from crude cell extracts and the like. Moreover, these antibodies are considered therapeutically useful to modulate the biological effect of DR5 or TRAIL-R3 proteins in vivo.

Methods and diagnostic systems for determining the levels of DR5 or TRAIL-R3 proteins in various tissue samples are also provided. These diagnostic methods can be used for monitoring the level of therapeutically administered DR5 or TRAIL-R3 proteins or fragments thereof to facilitate the maintenance of therapeutically effective amounts. These diagnostic methods can also be used to diagnose physiological disorders that result from abnormal levels or abnormal structures of the DR5 or TRAIL-R3 proteins.

BRIEF DESCRIPTION OF THE DRAWINGS

FIGS. 1A–1D illustrate sequence analysis and tissue distribution of DR5 and TRAIL-R3. Predicted amino acid sequence of human DR5 (A) and TRAIL-R3 (B). The mature DR5 and TRAIL-R3 are predicted to start at Glu+1 and Tyr+1 (indicated by black diamonds), respectively. The putative signal peptide and transmembrane domains are single- and double-underlined, respectively. The five identical repeats in the extracellular domain of TRAIL-R3 (B) are marked by black triangles. The intracellular cytoplasmic death domain of DR5 (A) is boxed. C, Colinear alignment of the death domains of members of the TNF receptor family. Identical residues in at least three out of six sequences are shaded. The death domain of DR5 is 64, 30, 30, 20, 31% identical to the corresponding domains in DR4, DR3, TNFR-1, Fas and CAR1 respectively.

FIGS. 2A and 2B illustrate that the extracellular domains of DR5 and TRAIL-R3 bind TRAIL and can block TRAIL-induced apoptosis as set forth in Example III herein.

FIGS. 3A–3F illustrate that expression of DR5 but neither TRAIL-R3 nor DR5s induces apoptosis in human cells as set forth in Example IV herein.

FIG. 5 illustrates the nucleotide and predicted amino acid sequence of the splice variant DR5s.

FIG. 6 illustrates a colinear alignment of DR5s and DR5. The dotted lines indicate sequences that are spliced in DR5 or DR5s.

DETAILED DESCRIPTION OF INVENTION

In accordance with the present invention, there are provided novel mammalian members of the TRAIL receptor protein family referred to herein as "DR5" and "TRAIL-R3", and active fragments thereof. DR5 is also referred to herein as "TRAIL-R2". As used herein, the phrases "DR5" and "TRAIL-R3" refer to isolated and/or substantially pure mammalian proteins, preferably human, that are able to bind to the cytotoxic ligand "TRAIL" (Wiley et al., 1995, Immunity, 3:673; and Marsters et al., 1996, Curr. Biol., 6:750), also known as Apo-2L. Invention DR5 and TRAIL-R3 proteins are further characterized by having the ability to mediate apoptosis. In their native environment, invention DR5 and TRAIL-R3 proteins are cell-surface receptor proteins.

Invention DR5 and TRAIL-R3 proteins include naturally occurring variants thereof encoded by mRNA generated by alternative splicing of a primary transcript (e.g., splice variant DR5s), and further including active fragments thereof which retain at least one native biological activity, such as, for example, the immunogenic ability to generate anti-DR5 or anti-TRAIL-R3 antibodies, the ability to bind TRAIL ligand, the ability to modulate apoptosis, and the like. In isolated form, invention isolated DR5 and TRAIL-R3 proteins are free of cellular components and/or contaminants normally associated with a native in vivo environment. As used herein, the term "polypeptide" refers to full length DR5 and TRAIL-R3 proteins or fragments thereof.

It has been found that DR5 but not TRAIL-R3, contains a cytoplasmic "death domain" necessary for induction of apoptosis, and engages the apoptotic pathway independent of the adaptor molecule FADD/Mort1. TRAIL-R3 on the other hand, can bind TRAIL but does not induce apoptosis, and thus is contemplated to function as an antagonistic receptor. Similarly, DR5s contains a truncated death domain of DR5 and thus also functions as an antagonistic decoy receptor.

Figure 1D:
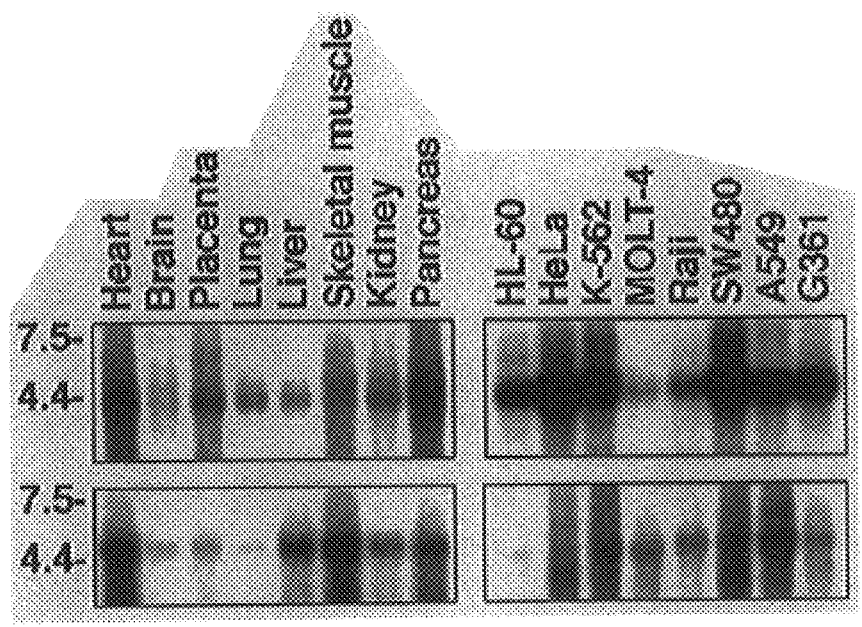

The invention DR5 proteins are further characterized by being expressed in at least the following cells: heart, brain, placenta, lung, liver, skeletal muscle, kidney and pancreas (see FIG. 1D and Example II). Other normal tissues such as testes, ovary, colon, small intestine and lymphoid tissues show detectable but low expression of DR5 transcript. In addition, DR5 mRNA transcript was detected in the following tumor cell lines: HL-60, promyelocytic leukemia; HeLa cell S3, K-562, chronic myelogenous leukemia; MOLT-4, lymphoblastic leukemia; Raji, Burkitt's lymphoma; SW480, colorectal adenocarcinoma; A549, lung carcinoma; G361, melanoma (FIG. 1D). Surprisingly, it was found that the amount of DR5 transcript is at least 100-fold higher in most tumor cell lines than in normal tissues. Thus, a correlation is contemplated between the high sensitivity of tumor cells to TRAIL and the elevated levels of DR5 in these cells.

Figure 3D:
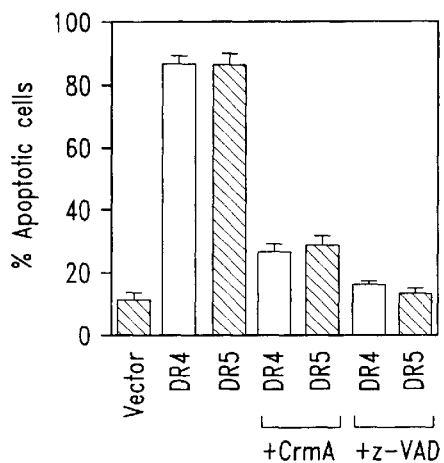
Figure 3E:
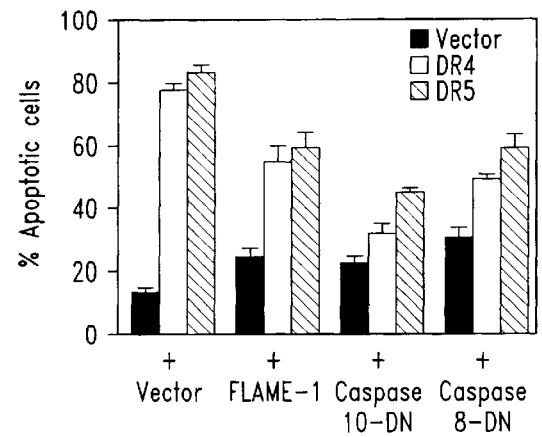

In addition, transient expression of DR5 triggers cytoplasmic death domain-dependent apoptosis (see FIGS. 3A and B). Similar to other TNF-receptor family members, DR5-induced apoptosis is efficiently blocked by the caspase inhibitors z-VAD-fmk and CrmA (FIG. 3D) and by the dominant negative inhibitors FLAME-I, caspase-8-DN and caspase-10-DN (FIG. 3E). Thus, it is contemplated herein that the upstream caspases-8 and -10 are involved in both the invention DR5 death signaling pathways. Moreover, unlike Fas, DR5 does not interact with the death-domain containing adaptor proteins FADD, CRADD, RIP or TRADD. Surprisingly, however, full length DR5, but not death domain-deleted mutants, are capable of forming complexes with caspase-8, caspase-10 and FLAME-1. Because these proteins do not interact directly, it is likely that the formation of these DR5-related complexes requires an adaptor molecule distinct from FADD.

In a particular embodiment of the present invention, an invention DR5 is a protein of 411 amino acids (SEQ ID NO:2) with an overall ~59% identity to DR4 (FIG. 1A). DR5's domain structure is highly related to DR4 and the other members of the TNF-receptor family. An invention DR5 contains a putative N-terminal signal peptide (amino acids −51 to −1 of FIG 1A) followed by an extracellular domain containing two cysteine-rich pseudorepeats. Following the extracellular domain is a transmembrane domain (amino acids 132-152 of FIG. 1A) and a cytoplasmic domain. Within the cytoplasmic domain there is a stretch of 67-amino acids (amino acids 273–339 of FIG. 1A) comprising a death domain homology region (FIG. 1C). The death domain of DR5 is 64, 30, 30, 20, 31% identical to the corresponding domains in DR4, DR3, TNFR-1, Fas and CAR1, respectively. Based on these criteria and its apoptotic activity (see Example IV below) the novel TRAIL-R2 protein is also designated death receptor-5 (DR5).

Figure 3F:
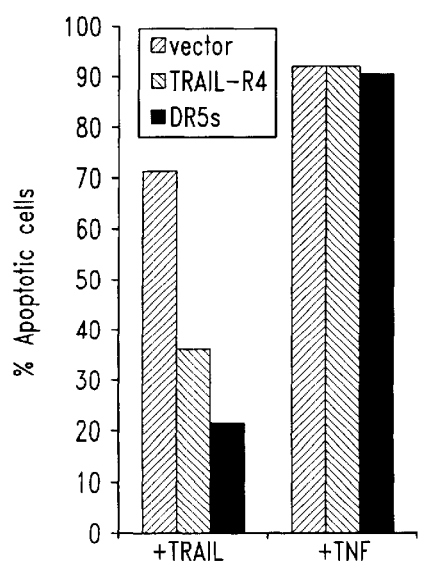

In an additional embodiment of the present invention splice variants are provided. Upon inspection of genomic clones of a TRAIL receptor, those skilled in the art are able to identify a variety of potential splice junctions. One such alternative splicing event yields DR5s which is an alternatively spliced isoform of DR5. DR5s is a protein of 350 amino acids (SEQ ID NO:6) which is encoded by a cDNA of 1053 nucleotides (SEQ ID NO:5). The mature DR5s protein contains a cytoplasmic region with a truncated death domain (FIGS. 5 and 6) that provides a protein having functionality opposite to that of DR5. To this end, DR5s substantially inhibits apoptosis by TRAIL, but not by TNF-α (FIG. 3F). Without wishing to be bound by theory, DR5s apparently acts as an inhibitory TRAIL-decoy receptor and thus may be able to protect cells against TRAIL-induced apoptosis.

The invention TRAIL-R3 proteins may be characterized as being expressed in at least the following cells: heart, brain, placenta, liver, skeletal muscle, kidney and pancreas (see FIG. 1D and Example II). In addition, TRAIL-R3 mRNA transcript was detected in the following tumor cell lines: HeLa cell S3, K-562, chronic myelogenous leukemia; MOLT-4, lymphoblastic leukemia; Raji, Burkitt's lymphoma; SW480, colorectal adenocarcinoma; A549, lung carcinoma; G361, melanoma (FIG. 1D). Surprisingly, relative to DR5 mRNA, a significantly elevated expression of TRAIL-R3 mRNA was observed in normal cells compared to tumor cells.

In addition, it has been found that transient expression of TRAIL-R3, which does not naturally contain a death domain, was incapable of inducing apoptosis (FIGS. 3A and B). Surprisingly, transient expression of TRAIL-R3 in MCF7 cells significantly blocked TRAIL-induced apoptosis (FIG. 3C), suggesting that TRAIL-R3 functions as an antagonistic decoy receptor.

Thus, since TRAIL-R3 does not contain a cytoplasmic death domain, and is capable of attenuating the cytotoxicity of TRAIL, TRAIL-R3 is contemplated as functioning physiologically as an antagonist to DR4 and DR5.

In a particular embodiment of the present invention, an invention TRAIL-R3 (SEQ ID NO:4) is a protein of 299 amino acids with an overall 40 and 36% identity to DR4 and DR5, respectively (FIG. 1B). This protein contains a putative N-terminal signal peptide (amino acids −63 to −1 of FIG. 1B) followed by an extracellular domain containing two cysteine-rich pseudorepeats and five nearly identical PAAEETMN (T) TSPGTPA repeats (amino acids 139–153, 154–168, 169–183, 184–198, and 199–213 of FIG. 1B, which corresponds to amino acids 202–216, 217–231, 232–246, 247–261, and 262–276 of SEQ ID NO:4). Following the extracellular domain is a C-terminal transmembrane domain (amino acids 217–236 of FIG. 1B). Unlike DR4 and DR5, this TRAIL-receptor does not contain a cytoplasmic domain. Based on these criteria and its ability to bind TRAIL (see Example III below), his protein is designated TRAIL-R3.

As used herein, the term "apoptosis" refers to the well-known process of programmed cell death. There is a variety of well-known, generally accepted in-vitro indicia of apoptosis, including nuclear morphological changes, internucleosomal fragmentation of DNA, the selective proteolysis of substrates, and the activation of CPP32-like caspases. For example, the substrates of the caspase family of cysteine proteases have received considerable attention because cleavage of these substrates offers molecular mechanisms for many of the hallmark morphological and functional changes exhibited by apoptotic cells (Casiano et al., *J. Exp. Med.* 184:765–770, (1996).

Use of the terms "isolated" and/or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant DNAs, RNAs, polypeptides and proteins of the invention are useful in ways described herein that the DNAs, RNAs, polypeptides or proteins as they naturally occur are not.

As used herein, "mammalian" refers to the variety of species from which invention DR5 or TRAIL-R3 proteins are derived, e.g., human, rat, mouse, rabbit, monkey, baboon, bovine, porcine, ovine, canine, feline, and the like.

Presently preferred DR5 and TRAIL-R3 proteins of the invention include amino acid sequences that are substantially the same as the protein sequence set forth in SEQ ID NO:2 and SEQ ID NO:4, respectively, as well as biologically active, modified forms thereof. Those of skill in the art will recognize that numerous residues of the above-described sequences can be substituted with other, chemically, sterically and/or electronically similar residues without substantially altering the biological activity of the resulting protein species. In addition, larger or smaller polypeptide sequences containing substantially the same sequence as SEQ ID NO:2 or SEQ ID NO:4 therein (e.g., splice variants including but not limited to SEQ ID NO:6, active fragments of AT, and the like) are contemplated.

As employed herein, the term "substantially the same amino acid sequence" refers to amino acid sequences having at least about 70% identity with respect to the reference amino acid sequence, and retaining comparable functional and biological activity characteristic of the protein defined by the reference amino acid sequence. Preferably, proteins having "substantially the same amino acid sequence" will have at least about 80%, more preferably 90% amino acid identity with respect to the reference amino acid sequence; with greater than about 95%, about 97%, about 99%, up to 100% amino acid sequence identity being especially preferred. Such amino acid sequence identity measurements may be determined by standard methodologies, including use of the National Center for Biotechnology Information BLAST search methodology available at www.ncbi.nlm.nih.gov. The identity methodologies most preferred are those described in U.S. Pat. No. 5,691,179 and Altschul et al., Nucleic Acids Res. 25:3389–3402, 1997, both of which are incorporated herein by reference. It is recognized, however, that DR5 and TRAIL-R3 proteins arising as splice variants (or DR5 and TRAIL-R3 nucleic acids referred to herein) containing less than the described levels of sequence identity or that are modified by conservative amino acid substitutions, or by substitution of degenerate codons, are also encompassed within the scope of the present invention. A preferred DR5 protein disclosed herein, is human DR5 set forth as SEQ ID NO:2. A preferred TRAIL-R3 protein disclosed herein, is human TRAIL-R3 set forth as SEQ ID NO:4. A preferred DR5 splice variant protein disclosed herein, is human DR5s, set forth as SEQ ID NO:6.

The term "biologically active" or "functional", when used herein as a modifier of invention DR5 and TRAIL-R3 proteins, or polypeptide fragment thereof, refers to a polypeptide that exhibits at least one of the functional characteristics attributed to TRAIL receptors. For example, one biological activity of invention DR5 and TRAIL-R3 proteins is the ability to bind to the TRAIL ligand. Other biological activities of invention DR5 and TRAIL-R3 proteins include the ability to modulate apoptosis (i.e., increasing or decreasing the level of apoptosis), the ability to bind intracellular adaptor proteins, and the like.

Yet another biological activity of invention DR5 or TRAIL-R3 proteins is the ability to act as an immunogen for the production of polyclonal and monoclonal antibodies that bind specifically to DR5 or TRAIL-R3. Thus, an invention nucleic acid encoding DR5 or TRAIL-R3 will encode a polypeptide specifically recognized by an antibody that also specifically recognizes the DR5 or TRAIL-R3 proteins (preferably human) including the sequences set forth in SEQ ID NO:2, SEQ ID NO:4, and SEQ ID NO:6. Such activity may be assayed by any method known to those of skill in the art. For example, a test polypeptide encoded by a DR5 or TRAIL-R3 cDNA can be used to produce antibodies, which may then be assayed for their ability to bind to the protein including the sequence set forth in SEQ ID NO:2, SEQ ID NO:4, or SEQ ID NO:6. If the antibody binds to the test-polypeptide and the protein including the sequence set forth in SEQ ID NO:2, SEQ ID NO:4, or SEQ ID NO:6 with substantially the same affinity, then the polypeptide possesses the required biological activity.

The invention DR5 or TRAIL-R3 proteins can be isolated by a variety of methods well-known in the art, e.g., the recombinant expression systems described herein, precipitation, gel filtration, ion-exchange, reverse-phase and affinity chromatography, and the like. Other well-known methods are described in Deutscher et al., *Guide to Protein Purification: Methods in Enzymology* Vol. 182, (Academic Press, (1990)), which is incorporated herein by reference. Alternatively, the isolated polypeptides of the present invention can be obtained using well-known recombinant methods as described, for example, in Sambrook et al., (supra., 1989).

An example of the means for preparing the invention polypeptide(s) is to express nucleic acids encoding the DR5 or TRAIL-R3 in a suitable host cell, such as a bacterial cell, a yeast cell, an amphibian cell (i.e., oocyte), or a mammalian cell, using methods well known in the art, and recovering the expressed polypeptide, again using well-known methods. Invention DR5 or TRAIL-R3 proteins may be isolated directly from cells that have been transformed with expression vectors as described herein. The invention polypeptide, biologically active fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

Also encompassed by the term DR5 or TRAIL-R3 are active fragments or polypeptide analogs thereof. The term "active fragment" refers to a peptide fragment hat is a portion of a full length DR5 or TRAIL-R3 protein, provided that the portion has a biological activity, as defined above, that is characteristic of at least one function of the corresponding full length protein. For example, an active fragment of an DR5 or TRAIL-R3 protein, such as an extracellular domain can have an activity such as the ability, for example, to bind TRAIL ligand or to modulate the level of apoptosis after binding to TRAIL. The characteristic of an active fragment of invention DR5 or TRAIL-R3 proteins to elicit an immune response is useful for obtaining an anti-TRAIL receptor antibody. Thus, the invention also provides active fragments of invention DR5 and TRAIL-R3 proteins, which can be identified using the binding and bioassays described herein.

The term "polypeptide analog" includes any polypeptide having an amino acid residue sequence substantially identical to a sequence specifically shown herein in which one or more residues have been conservatively substituted with a functionally similar residue and which displays the ability to mimic DR5 or TRAIL-R3 as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The amino acid length of active fragments or polypeptide analogs of the present can range from about 5 amino acids up to the full-length protein sequence of DR5 or TRAIL-R3. In certain embodiments, the amino acid lengths include, for example, at least about 10 amino acids, at least about 20, at least about 30, at least about 40; at least about 50, at least about 75, at least about 100, at least about 150, at least about 200, at least about 250 or more amino acids in length up to the fill-length DR5 or TRAIL-R3 protein sequence.

As used herein the phrase "conservative substitution" also includes the use of a chemically derivatized residue in place of a non-derivatized residue, provided that such polypeptide displays the required binding activity. The phrase "chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; S-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions of residues, relative to the sequence of a polypeptide whose sequence is shown herein, so long as the required activity is maintained.

The present invention also provides compositions containing an acceptable carrier and any of an isolated, purified DR5 or TRAIL-R3 polypeptide, an active fragment or polypeptide analog thereof, or a purified, mature protein and active fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents.

In accordance with another embodiment of the present invention, there are provided isolated nucleic acids, which encode invention DR5 or TRAIL-R3 proteins, and fragments thereof. The nucleic acid molecules described herein are useful for producing invention proteins, when such nucleic acids are incorporated into a variety of protein expression systems known to those of skill in the art. In addition, such nucleic acid molecules or fragments thereof can be labeled with a readily detectable substituent for use as hybridization probes to assay for the presence and/or amount of an DR5 or TRAIL-R3 gene or mRNA transcript in a given sample. The nucleic acid molecules described herein, and fragments thereof, are also useful as primers and/or templates in a PCR reaction for amplifying genes encoding the invention protein described herein.

The term "nucleic acid" (also referred to as polynucleotides) encompasses ribonucleic acid (RNA) or deoxyribonucleic acid (DNA), probes, oligonucleotides, and primers. DNA can be either complementary DNA (cDNA) or genomic DNA, e.g. a gene encoding an DR5 or TRAIL-R3 protein. One means of isolating a nucleic acid encoding a DR5 or TRAIL-R3 polypeptide is to probe a mammalian genomic or cDNA library with a natural or artificially designed DNA probe using methods well known in the art. DNA probes derived from nucleic acid encoding DR5 or TRAIL-R3 proteins are particularly useful for this purpose. DNA and cDNA molecules that encode DR5 or TRAIL-R3 proteins can be used to obtain complementary genomic DNA, cDNA or RNA from mammalian (e.g., human, mouse, rat, rabbit, pig, and the like), or other animal sources, or to isolate related cDNA or genomic clones by the screening of cDNA or genomic libraries, by methods described in more detail below. Such nucleic acids may include, but are not limited to, nucleic acids having substantially the same nucleotide sequence as set forth in SEQ ID NO: I or SEQ ID NO:3, or splice variant cDNA sequences thereof.

Also encompassed by the terms DR5 or TRAIL-R3 may be "splice variant" or "alternatively spliced" proteins thereof. These terms are used herein to describe a particular nucleotide sequence encoding an invention receptor and refers to a cDNA sequence or protein encoded thereby that results from the well known eukaryotic RNA splicing process. The RNA splicing process may involve the removal of introns and the joining of exons from eukaryotic primary RNA transcripts to create mature RNA molecules of the cytoplasm. Methods of isolating splice variant nucleotide sequences are well known in the art. For example, one skilled in the art can employ nucleotide probes derived from the DR5 or TRAIL-R3 encoding cDNA of SEQ ID NO:1 or SEQ ID NO:3 to screen a cDNA or genomic library as described herein. A referred splice variant is the alternatively spliced isoform of DR5, or DR5short DR5s). The cDNA encoding this splice variant is set forth in SEQ ID NO:5.

Alternative splicing may play an important role in regulation of apoptosis. For example, alternative splicing of the Bcl-x, Ced-4, and Ich-1 pre-mRNA produces products that play opposite roles in apoptosis. In this regard, as described herein, DR5s may be similar in that this isoform may be capable of inhibiting apoptosis while the larger form (DR5) may promote apoptosis (see FIG. 3F).

In one embodiment of the present invention, cDNAs encoding the invention DR5 and TRAIL-R3 proteins disclosed herein include substantially the same nucleotide sequence as set forth in SEQ ID NO:1, SEQ ID NO:3, and SEQ ID NO:5.

As employed herein, the term "substantially the same nucleotide sequence" refers to DNA having sufficient identity to the reference polynucleotide, such that it hybridizes to the reference nucleotide under moderately stringent hybridization conditions. In one embodiment, DNA having substantially the same nucleotide sequence as the reference nucleotide sequence encodes substantially the same amino acid sequence as that set forth in SEQ ID NO:2, SEQ ID NO:4, or SEQ ID NO:6 or a larger amino acid sequence including SEQ ID NO:2, SEQ ID NO:4, or SEQ ID NO:6. In another embodiment, DNA having "substantially the same nucleotide sequence" as the reference nucleotide sequence has at least 60% identity with respect to the reference nucleotide sequence. DNA having at least 70%, at least 80%, more preferably at least 90%, yet more preferably at least 95%, with up to at least 97%, and at least 99% identity to the reference nucleotide sequence is preferred.

The present invention also encompasses nucleic acids that differ from the nucleic acids shown in SEQ ID NO: 1, SEQ ID NO:3, or SEQ ID NO:5, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that function in substantially the same manner to produce the same protein product(s) as the nucleic acids disclosed herein. In particular, functionally equivalent nucleic acids may encode polypeptides that are the same as those disclosed herein or that have conservative amino acid variations, or that encode larger polypeptides that include SEQ ID NO:2, SEQ ID NO:4, or SEQ ID NO:6. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding DR5 and TRAIL-R3 proteins that, by virtue of the degeneracy of the genetic code, do not necessarily hybridize to the invention nucleic acids under specified hybridization conditions. Preferred nucleic acids encoding the invention DR5 or TRAIL-R3 polypeptide are comprised of nucleotides that encode substantially the same amino acid sequence set forth in SEQ ID NO:2, SEQ ID NO:4, or splice variants thereof, respectively.

Thus, an exemplary nucleic acid encoding an invention DR5 or TRAIL-R3 protein may be selected from:

(a) DNA encoding the amino acid sequence set forth in SEQ ID NO:2 or SEQ ID NO:4;

(b) DNA that hybridizes to the DNA of (a) under moderately stringent conditions, wherein said DNA encodes biologically active DR5 or TRAIL-R3; or (c) DNA degenerate with respect to either (a) or (b) above, wherein said DNA encodes biologically active DR5 or TRAIL-R3.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those skilled in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5X Denhart's solution, 5X SSPE, 0.2% SDS at 42° C., followed by washing in 0.5X SSPE, 0.2% SDS, at 42° C.

The phrase "high stringency hybridization" refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5X Denhart's solution, 5X SSPE, 0.2% SDS at 42° C., followed by washing in 0.1X SSPE, and 0.1% SDS at 65° C.

The phrase "low stringency hybridization" refers to conditions equivalent to hybridization in 10% formamide, 5X Denhart's solution, 6X SSPE, 0.2% SDS at 37° C., followed by washing in 1X SSPE, 0.2% SDS, at 50° C. Denhart's solution and SSPE (see, e.g., Sambrook et al., *Molecular Cloning, A Laboratory Manual,* Cold Spring Harbor Laboratory Press, 1989) are well known to those of skill in the art as are other suitable hybridization buffers.

As used herein, the term "degenerate" refers to codons that differ in at least one nucleotide from a reference nucleic acid, e.g., SEQ ID NO:1, SEQ ID NO:3, or SEQ ID NO:5, but encode the same amino acids as the reference nucleic acid. For example, codons specified by the triplets "UCU", "UCC", "UCA", and "UCG" are degenerate with respect to each other since all four of these codons encode the amino acid serine.

Preferred nucleic acids encoding the invention polypeptide(s) hybridize under moderately stringent, preferably high stringency, conditions to substantially the entire sequence of the nucleic acid sequence set forth in SEQ ID NO:1, SEQ ID NO:3, or SEQ ID NO:5.

Site-directed mutagenesis of any region of DR5 or TRAIL-R3 cDNA is contemplated herein for the production of mutant DR5 or TRAIL-R3 cDNAs. For example, the Transformer Mutagenesis Kit (available from Clontech, Palo Alto, Calif.) can be used to construct a variety of missense and/or nonsense mutations to DR5 or TRAIL-R3 cDNA, and the like.

The invention nucleic acids may be produced by a variety of methods well-known in the art, e.g., the methods described herein, employing PCR amplification using oligonucleotide primers from various regions of SEQ ID NO:1 or SEQ ID NO:3, and the like.

In accordance with a further embodiment of the present invention, optionally labeled DR5-encoding and TRAIL-R3-encoding cDNAs, or fragments thereof, can be employed to probe library(ies) (e.g., cDNA, genomic, and the like) for additional nucleic acid sequences encoding related novel mammalian DR5 and TRAIL-R3 proteins. Construction of mammalian cDNA and genomic libraries, preferably a human library, is well-known in the art.

Screening of such a cDNA or genomic library is initially carried out under low-stringency conditions, which comprise a temperature of less than about 42° C., a formamide concentration of less than about 50%, and a moderate to low salt concentration.

In one embodiment, probe-based screening conditions comprise a temperature of about 37° C., a formamide concentration of about 20%, and a salt concentration of about 5X standard saline citrate (SSC; 20X SSC contains 3M sodium chloride, 0.3M sodium citrate, pH 7.01). Such conditions will allow the identification of sequences which have a substantial degree of similarity with the probe sequence, without requiring perfect homology. The phrase "substantial similarity" refers to sequences which share at least 50% homology. Preferably, hybridization conditions will be selected which allow the identification of sequences having at least 70% homology with the probe, while discriminating against sequences which have a lower degree of homology with the probe. As a result, nucleic acids having substantially the same (i.e., similar) nucleotide sequence as SEQ ID NO:1, SEQ ID NO:3, or splice variants thereof including SEQ ID NO:5, are obtained.

As used herein, a nucleic acid "oligonucleotide", also referred to herein as a probe or primer, is single-stranded DNA or RNA, or analogs thereof, that has a sequence of nucleotides that includes, for example, at least 14, at least 20, at least 50, at least 100, at least 200, at least 300, at least 400, or at least 500 contiguous nucleotide bases that are the same as (or the complement of) any contiguous bases set forth in any of SEQ ID NO:1 or SEQ ID NO:3. Preferred regions from which to construct probes include 5' and/or 3' coding regions of SEQ ID NO:1, SEQ ID NO:3, or splice variants thereof. In addition, the entire cDNA encoding region of an invention protein, such as the entire sequence corresponding to SEQ ID NO:1 (DR5) or SEQ ID NO:3 (TRAIL-R3), may be used as a probe. Further, when probing a splice variant, the splice junctions or intervening sequences may be used to construct a probe (see FIG. 6). Probes may be labeled by methods well-known in the art, as described hereinafter, and used in various diagnostic kits.

As used herein, the terms "label" and "indicating means" in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry.

Also provided are antisense oligonucleotides having a sequence capable of binding specifically with any portion of an mRNA that encodes DR5 or TRAIL-R3 proteins so as to prevent translation of the mRNA. The antisense oligonucleotide may have a sequence capable of binding specifically with any portion of the sequence of the cDNA encoding DR5 or TRAIL-R3 proteins. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense oligonucleotide is an antisense oligonucleotide comprising chemical analogs of nucleotides.

Compositions comprising an amount of the antisense oligonucleotide, described above, effective to reduce expression of DR5 or TRAIL-R3 proteins by passing through a cell membrane and binding specifically with mRNA encoding DR5 or TRAIL-R3 proteins so as to prevent translation and an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. The structure may be part of a protein known to bind to a cell-type specific receptor, e.g., FGF and other growth factors.

Antisense oligonucleotide compositions are useful to inhibit translation of mRNA encoding invention polypeptides. Synthetic oligonucleotides, or other antisense chemical structures are designed to bind to mRNA encoding DR5 or TRAIL-R3 proteins and inhibit translation of mRNA and are useful as compositions to inhibit expression of DR5 or TRAIL-R3 associated genes in a tissue sample or in a subject.

In accordance with another embodiment of the invention, kits are provided for detecting the presence of a DR5 or TRAIL-R3 nucleic sequence comprising at least one oligonucleotide, e.g., a probe or antisense oligonucleotide, according to the present invention. Such kits can be used for detecting mutations, duplications, deletions, splice variant transcripts, rearrangements or aneuploidies in a DR5 or TRAIL-R3 gene.

The present invention provides means to modulate levels of expression of DR5 or TRAIL-R3 proteins by employing synthetic antisense oligonucleotide compositions (hereinafter SAOC) which inhibit translation of mRNA encoding these polypeptides. Synthetic oligonucleotides, or other antisense chemical structures designed to recognize and selectively bind to mRNA, are constructed to be complementary to portions of the DR5 or TRAIL-R3 coding strand or nucleotide sequences shown in SEQ ID NO:1 or SEQ ID NO:3. The SAOC is designed to be stable in the blood stream for administration to a subject by injection or by direct tumor site integration, or stable in laboratory cell culture conditions. The SAOC is designed to be capable of passing through the cell membrane in order to enter the cytoplasm of the cell by virtue of physical and chemical properties of the SAOC which render it capable of passing through cell membranes, for example, by designing small, hydrophobic SAOC chemical structures, or by virtue of specific transport systems in the cell which recognize and transport the SAOC into the cell. In addition, the SAOC can be designed for administration only to certain selected cell populations by targeting the SAOC to be recognized by specific cellular uptake mechanisms which bind and take up the SAOC only within select cell populations.

For example, the SAOC may be designed to bind to a receptor found only in a certain cell type, as discussed supra. The SAOC is also designed to recognize and selectively bind to target mRNA sequence, which may correspond to a sequence contained within the sequence shown in SEQ ID NO: 1, SEQ ID NO:3, or splice variants thereof. The SAOC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SAOCs have been shown to be capable of such properties when directed against mRNA targets (see Cohen et al., *TIPS,* 10:435 (1989) and Weintraub, *Sci. American,* January (1990), p.40; both incorporated herein by reference).

In accordance with yet another embodiment of the present invention, there is provided a method for the recombinant production of invention DR5 or TRAIL-R3 proteins by expressing the above-described nucleic acid sequences in suitable host cells. Recombinant DNA expression systems that are suitable to produce DR5 and TRAIL-R3 proteins described herein are well-known in the art. For example, the above-described nucleotide sequences can be incorporated into vectors for further manipulation. As used herein, vector (or plasmid) refers to discrete elements that are used to introduce heterologous DNA into cells for either expression or replication thereof.

Suitable expression vectors are well-known in the art, and include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that are replicable in eukaryotic cells and/or prokaryotic cells and those that remain episomal or those which integrate into the host cell genome. In addition, vectors may contain appropriate packaging signals that enable the vector to be packaged by a number of viral virions, e.g., retroviruses, herpes viruses, adenoviruses, resulting in the formation of a "viral vector."

As used herein, the term "operatively linked" refers to the functional relationship of DNA with regulatory and effector nucleotide sequences, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA.

Suitable transformation vectors are well-known in the art and include Blueskript and phage Lambda ZAP vectors (Stratagene, La Jolla, Calif.), and the like. Other suitable vectors and promoters are disclosed in detail in U.S. Pat. No. 4,798,885, issued Jan. 17, 1989, the disclosure of which is incorporated herein by reference in its entirety.

In accordance with another embodiment of the present invention, there are provided "recombinant cells" containing the nucleic acid molecules (i.e., DNA or mRNA) of the present invention. Methods of transforming suitable host cells, preferably bacterial cells, and more preferably *E. coli* cells, as well as methods applicable for culturing said cells containing a gene encoding a heterologous protein, are generally known in the art. See, for example, Sambrook et al., *Molecular Cloning: A Laboratory Manual* (2 ed.), Cold Spring Harbor Laboratory Press, Cold Spring Harbor, N.Y., USA (1989).

Exemplary methods of introducing (transducing) expression vectors containing invention nucleic acids into host cells to produce transduced recombinant cells (i.e., cells containing recombinant heterologous nucleic acid) are well-known in the art (see, for review, Friedmann, *Science*, 244:1275–1281 (1989); Mulligan, Science, 260:926–932 (1993), each of which are incorporated herein by reference in their entirety). Exemplary methods of transduction include, e.g., infection employing viral vectors (see, e.g., U.S. Pat. Nos. 4,405,712 and 4,650,764), calcium phosphate transfection (U.S. Pat. Nos. 4,399,216 and 4,634,665), dextran sulfate transfection, electroporation, lipofection (see, e.g., U.S. Pat. Nos. 4,394,448 and 4,619,794), cytofection, particle bead bombardment, and the like. The heterologous nucleic acid can optionally include sequences which allow for its extrachromosomal (i.e., episomal) maintenance, or the heterologous DNA can be caused to integrate into the genome of the host (as an alternative means to ensure stable maintenance in the host).

Host organisms contemplated for use in the practice of the present invention include those organisms in which recombinant production of heterologous proteins has been carried out. Examples of such host organisms include bacteria (e.g., *E. coli*), yeast (e.g., *Saccharomyces cerevisiae, Candida tropicalis, Hansenula polymorpha* and *P. pastoris;* see, e.g., U.S. Pat. Nos. 4,882,279, 4,837,148, 4,929,555 and 4,855,231), mammalian cells (e.g., HEK293, CHO and Ltk- cells), insect cells, and the like.

In one embodiment, nucleic acids encoding the invention DR5 or TRAIL-R3 proteins can be delivered into mammalian cells, either in vivo or in vitro using suitable viral vectors well-known in the art (e.g., retroviral vectors, adenovirus vectors, and the like). In addition, where it is desirable to limit or reduce the in vivo expression of the invention DR5 or TRAIL-R3 proteins, the introduction of the anti-sense strand of the invention nucleic acid is contemplated.

Viral based systems provide the advantage of being able to introduce relatively high levels of the heterologous nucleic acid into a variety of cells. Suitable viral vectors for introducing invention nucleic acid encoding an DR5 or TRAIL-R3 protein into mammalian cells (e.g., vascular tissue segments) are well known in the art. These viral vectors include, for example, Herpes simplex virus vectors (e.g., Geller et al., *Science*, 241:1667–1669 (1988)), Vaccinia virus vectors (e.g., Piccini et al., *Meth. in Enzymology,* 153:545–563 (1987); Cytomegalovirus vectors (Mocarski et al., in Viral Vectors, Y. Gluzman and S. H. Hughes, Eds., Cold Spring Harbor Laboratory, Cold Spring Harbor, N.Y., 1988, pp. 78–84), Moloney murine leukemia virus vectors (Danos et al., *PNAS. USA,* 85:6469 (1980)), adenovirus vectors, (e.g., Logan et al., *PNAS, USA.* 81:3655–3659 (1984); Jones et al., *Cell,* 17:683–689 (1979); Berkner, *Biotechniques,* 6:616–626 (1988); Cotten et al.,*PNAS, USA,* 89:6094–6098 (1992); Graham et al., *Meth. Mol. Biol,* 7:109–127 (1991)), adeno-associated virus vectors, retrovirus vectors (see, e.g., U.S. Pat. Nos. 4,405,712 and 4,650,764), and the like. Especially preferred viral vectors are the adenovirus and retroviral vectors.

For example, in one embodiment of the present invention, adenovirus-transferrin/polylysine-DNA (TfAdpl-DNA) vector complexes (Wagner et al., *PNAS, USA,* 89:6099–6103 (1992); Curiel et al., *Hum. Gene Therapy,* 3:147–154 (1992); Gao et al., *Hum. Gene Ther.,* 4:14–24 (1993)) are employed to transduce mammalian cells with heterologous DR5 or TRAIL-R3 nucleic acid. Any of the plasmid expression vectors described herein may be employed in a TfAdpl-DNA complex.

As used herein, "retroviral vector" refers to the well-known gene transfer plasmids that have an expression cassette encoding an heterologous gene residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. No. 5,252,479, and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, the mouse mammary tumor virus vectors (e.g., Shackleford et al., *PNAS. USA,* 85:9655–9659 (1988)), and the like.

In accordance with yet another embodiment of the present invention, there are provided anti-DR5 and anti -TRAIL-R3 antibodies having specific reactivity with DR5 and TRAIL-R3 proteins, respectively, of the present invention. Active fragments of antibodies are encompassed within the definition of "antibody". Invention antibodies can be produced by methods known in the art using invention DR5 or TRAIL-R3 proteins, or portions thereof as antigens. For example, polyclonal and monoclonal antibodies can be produced by methods well known in the art, as described, for example, in Harlow and Lane, *Antibodies: A Laboratory Manual* (Cold Spring Harbor Laboratory (1988)), which is incorporated herein by reference.

Invention DR5 and TRAIL-R3 proteins can be used as immunogens in generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., *Trends Pharmacol. Sci.* 12:338 (1993); Ausubel et al., *Current Protocols in Molecular Biology* (John Wiley and Sons, NY (1989) which are incorporated herein by reference).

Antibody so produced can be used, inter alia, in diagnostic methods and systems to detect the level of DR5 or TRAIL-R3 protein present in a mammalian, preferably human, body sample, such as tissue or vascular fluid. Such antibodies can also be used for the immunoaffinity or affinity chromatography purification of the invention DR5 and TRAIL-R3 proteins. In addition, methods are contemplated herein for detecting the presence of DR5 or TRAIL-R3 proteins either on the surface of a cell or within a cell, which methods comprise contacting the cell with an antibody that specifically binds to DR5 or TRAIL-R3 proteins, under conditions permitting binding of the antibody to DR5 or TRAIL-R3 proteins, detecting the presence of the antibody bound to DR5 or TRAIL-R3, and thereby detecting the presence of invention polypeptides on the surface of, or within, the cell. With respect to the detection of such polypeptides, the antibodies can be used for in vitro diagnostic or in vivo imaging methods.

Immunological procedures useful for in vitro detection of target DR5 or TRAIL-R3 proteins in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

Invention anti-DR5 or TRAIL-R3 antibodies are contemplated for use herein to modulate activity of the DR5 or TRAIL-R3 polypeptide in living animals, in humans, or in biological tissues or fluids isolated therefrom. The term "modulate" refers to a compound's ability to increase (e.g., via an agonist) or inhibit (e.g., via an antagonist) the biological activity of DR5 or TRAIL-R3 protein, such as the apoptosis mediating activity of DR5 or TRAIL-R3. Accordingly, compositions comprising a carrier and an amount of an antibody having specificity for DR5 or TRAIL-R3 proteins effective to block naturally occurring ligands, such as TRAIL, or other DR5-binding or TRAIL-binding proteins from binding to invention DR5 or TRAIL-R3 proteins are contemplated herein. For example, a monoclonal antibody directed to an epitope of DR5 or TRAIL-R3 present on the surface of a cell that has an amino acid sequence substantially the same as an amino acid sequence shown in SEQ ID NO:2, SEQ ID NO:4, or splice variant thereof (e.g., SEQ ID NO:6), can be useful for this purpose.

The present invention further provides transgenic non-human mammals that are capable of expressing exagenous nucleic acids encoding DR5 or TRAIL-R3 proteins. As employed herein, the phrase "exagenous nucleic acid" refer to nucleic acid sequence which is not native to the host, or which is present in the host in other than its native environment (e.g., as part of a genetically engineered DNA construct). In addition to naturally occurring levels of invention TRAIL receptors, invention DR5 or TRAIL-R3 proteins can either be overexpressed, underexpressed, or expressed in an inactive mutated form (such as in the well-known knockout transgenics) in transgenic mammals.

Also provided are transgenic non-human mammals capable of expressing nucleic acids encoding DR5 or TRAIL-R3 proteins so mutated as to be incapable of normal activity, i.e., do not express native DR5 or TRAIL-R3. The present invention also provides transgenic non-human mammals having a genome comprising antisense nucleic acids complementary to nucleic acids encoding DR5 or TRAIL-R3 proteins, placed so as to be transcribed into antisense mRNA complementary to mRNA encoding DR5 or TRAIL-R3 proteins, which hybridizes to the mRNA and, thereby, reduces the translation thereof. The nucleic acid may additionally comprise an inducible promoter and/or tissue specific regulatory elements, so that expression can be induced, or restricted to specific cell types. Examples of nucleic acids are DNA or cDNA having a coding sequence substantially the same as the coding sequence shown in SEQ ID NO:1, SEQ ID NO:3, or SEQ ID NO:5. An example of a non-human transgenic mammal is a transgenic mouse.

Animal model systems which elucidate the physiological and behavioral roles of DR5 or TRAIL-R3 proteins are also provided, and are produced by creating transgenic animals in which the expression of the DR5 or TRAIL-R3 polypeptide is altered using a variety of techniques. Examples of such techniques include the insertion of normal or mutant versions of nucleic acids encoding a DR5 or TRAIL-R3 polypeptide by microinjection, retroviral infection or other means well known to those skilled in the art, into appropriate fertilized embryos to produce a transgenic animal. (See, for example, Hogan et al., *Manipulating the Mouse Embryo: A Laboratory Manual* (Cold Spring Harbor Laboratory, (1986)).

Also contemplated herein, is the use of homologous recombination of mutant or normal versions of genes encoding DR5 or TRAIL-R3 proteins with the native gene locus in transgenic animals, to alter the regulation of expression or the structure of (see, Capecchi et al., *Science,* 244:1288 (1989); Zimmer et al., *Nature,* 338:150 (1989); which are incorporated herein by reference). Homologous recombination techniques are well known in the art. Homologous recombination replaces the native (endogenous) gene with a recombinant or mutated gene to produce an animal that cannot express native (endogenous) protein but can express, for example, a mutated protein which results in altered expression of DR5 or TRAIL-R3 proteins.

In contrast to homologous recombination, microinjection adds genes to the host genome, without removing host genes. Microinjection can produce a transgenic animal that is capable of expressing both endogenous and exagenous DR5 or TRAIL-R3 protein. Inducible promoters can be linked to the coding region of nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific agents, i.e., agonists and antagonists, which activate or inhibit protein responses.

Invention nucleic acids, oligonucleotides (including antisense), vectors containing same, transformed host cells, polypeptides and combinations thereof, as well as antibodies of the present invention, can be used to screen compounds in vitro to determine whether a compound functions as a potential agonist or antagonist to invention DR5 or TRAIL-R3 proteins. These in vitro screening assays provide information regarding the function and activity of invention DR5 or TRAIL-R3 proteins, which can lead to the identification and design of compounds that are capable of specific interaction with one or more types of polypeptides, peptides or proteins.

Apoptosis plays a significant role in numerous pathological conditions in that programmed cell death is either inhibited, resulting in increased cell survival, or enhanced which results in the loss of cell viability. Examples of pathological conditions resulting from increased cell survival include cancers such as lymphomas, carcinomas and hormone dependent tumors. Such hormone dependent tumors include, for example, breast, prostate and ovarian cancer. Autoimmune diseases such as systemic lupus erythematosus and immune-mediated glomerulonephritis as well as viral infections such as herpes virus, poxvirus and adenovirus also result from increased cell survival or the inhibition of apoptosis.

In contrast, apoptotic diseases where enhanced programmed cell death is a prevalent cause generally includes, for example, degenerative disorders such as Alzheimer's disease, Parkinson's disease, Amyotrophic lateral sclerosis, Retinitis pigmentosa, and Cerebellar degeneration. Other diseases associated with increased apoptosis include, for example, myelodysplastic syndromes such as aplastic anemia and ischemic injury including myocardial infarction, stroke and reperfusion injury.

The DR5 or TRAIL-R3 encoding nucleic acids and polypeptides of the invention can be used to diagnose, treat or reduce the severity of cell death mediated diseases such as those described above as well as other diseases mediated by either increased or decreased programmed cell death. Additionally, the DR5 or TRAIL-R3 encoding nucleic acids and polypeptides of the invention can be used to screen for pharmaceutical compounds and macromolecules which inhibit or promote DR5 or TRAIL-R3 mediated apoptosis.

For example, the DR5 or TRAIL-R-3 encoding nucleic acids, polypeptides and functional fragments thereof can be used to diagnose, or to generate reagents to diagnose diseases mediated or characterized by programmed cell death. Diagnosis can be by nucleic acid probe hybridization with DR5 or TRAIL-R3 containing nucleotide sequences, antibody or ligand mediated detection with DR5 or TRAIL-R3 binding agents or by enzyme catalysis of detectable DR5 or TRAIL-R3 substrates. Such methods are routine to those skilled in the art. Detection can be performed ex vivo, for example, by removing a cell or tissue sample from an individual exhibiting or suspected of exhibiting a cell death mediated disease. Correlation of increased DR5 or TRAIL-R3 expression or activity may be indicative of diseases characterized by enhanced programmed cell death whereas correlation of decreased DR5 or TRAIL-R3 expression or activity may be indicative of diseases characterized by the inhibition of programmed cell death.

Thus, in accordance with still another embodiment of the present invention, there is provided a method for identifying compounds that may bind to DR5 or TRAIL-R3 proteins such as, for example, antibodies, binding agents, and the like. For example, the invention DR5 or TRAIL-R3 proteins may be employed in a competitive binding assay. Such an assay can accommodate the rapid screening of a large number of compounds to determine which compounds, if any, are capable of binding to DR5 or TRAIL-R3 proteins. Subsequently, more detailed assays can be carried out with those compounds found to bind, to further determine whether such compounds act as modulators, e.g., agonists or antagonists, of invention proteins.

Thus, in another embodiment of the invention, there is provided a bioassay for identifying compounds that modulate the activity of invention DR5 or TRAIL-R3 proteins. According to this method, invention DR5 or TRAIL-R3 proteins, preferably membrane bound, may be contacted with TRAIL ligand in the presence and in the absence of a test-compound; the activity of the DR5 or TRAIL-R3 proteins is monitored subsequent to the contact with the test compound, and those test-compounds that may cause either the increase or decrease of apoptosis in cellular systems having membrane bound DR5 or TRAIL-R3 proteins therein may be identified as functional agents for modulating DR5 or TRAIL-R3 proteins.

In accordance with another embodiment of the present invention, transformed host cells (either completely-intact or semi-intact cells) that recombinantly express invention DR5 or TRAIL- R3 proteins can be contacted with a test compound, and the modulating effect(s) thereof can then be evaluated by comparing the relative levels of apoptosis modulation in the presence and absence of test compound, or by comparing the response of test cells or control cells (i.e., cells that do not express DR5 or TRAIL-R3 proteins), to the presence of the compound.

As used herein, a compound or a signal that "modulates the activity" of invention DR5 or TRAIL-R3 proteins refers to a compound or a signal that may alter the activity of DR5 or TRAIL-R3 proteins so that the activity of the invention DR5 or TRAIL-R3 proteins is different in the presence of the compound or signal than in the absence of the compound or signal. In particular, such compounds or signals include agonists and antagonists. An agonist encompasses a compound or a signal that may activate or increase the function of invention DR5 or TRAIL-R3 proteins. Alternatively, an antagonist includes a compound or signal that may interfere with, inhibit or otherwise decrease DR5 or TRAIL-R3 protein function. Typically, the effect of an antagonist may be observed as a blocking of agonist-induced protein activation. Antagonists include competitive and non-competitive antagonists. A competitive antagonist (or competitive blocker) interacts with or near the site specific for TRAIL binding. A non-competitive antagonist or blocker inactivates the function of the polypeptide by interacting with a site other than the apoptosis modulating region of invention DR5 or TRAIL-R3 proteins.

As understood by those of skill in the art, assay methods for identifying compounds that modulate DR5 or TRAIL-R3 activity generally require comparison to a control. One type of a "control" is a cell or culture that is treated substantially the same as the test cell or test culture exposed to the compound, with the distinction that the "control" cell or culture is not exposed to the compound. For example, a type of "control" cell or culture may be a cell or culture that is identical to the transfected cells, with the exception that the "control" cell or culture do not express native proteins. Accordingly, the response of the transfected cell to compound may be compared to the response (or lack thereof) of the "control" cell or culture to the same compound under the same reaction conditions.

In another embodiment of the present invention, there is provided a bioassay for evaluating whether test compounds are capable of acting as agonists or antagonists for DR5 or TRAIL-R3 proteins, wherein said bioassay comprises:

(a) culturing cells containing: DNA which expresses a TRAIL receptor selected from DR5 or TRAILR3, or functional modified forms thereof, wherein said culturing is carried out in the presence of at least one compound whose ability to modulate apoptotic activity of TRAIL receptors is sought to be determined, and thereafter (b) monitoring said cells for either an increase or decrease in the level of apoptosis.

Such an assay can be carried out in the presence or absence of TRAIL ligand. Methods are well-known in the art for measuring apoptosis can be employed in bioassays described herein to identify agonists and antagonists of DR5 or TRAIL-R3 proteins. For example, the methods described in Example IV can be used to evaluate the apoptotic activity of recombinant DR5 or TRAIL-R3 proteins or mutants and/or analogs thereof, expressed in mammalian host cells.

In addition, the occurrence of apoptosis in cell-free systems can be assessed by detecting the relative levels of: caspase processing (i.e., the cleavage of the pro-caspase to active forms; see, e.g., Casciola-Rosen et al., 1996, *J. Exp. Med.,*183:1957-1964; Tewari et al, 1995, *J. Biol. Chem.,*

32:18738–18741; Tewari et al, 1995, *Cell,* 81:801–809), caspase activation, cytosolic substrate cleavage, the release of cytochrome-c from mitochondria, and the like. Exemplary cytosolic substrates that are cleaved as a result of apoptosis are set forth in Table 1, and include: fodrin, CPP32, PKCδ, and the like.

When nuclei are present in the bioassays described herein, the occurrence of apoptosis can be assessed by, in addition to the methods described above, detecting: chromatin condensation, shrinkage and fragmentation of the nuclei, and the like (see, for example, Zanzami et al., *J. Exp. Med.,* 183:1533–1544 (1995); Newmeyer et al., *Cell,* 79:353–364 (1994)). In addition, nuclear substrates that are cleaved as a result of apoptosis are also set forth in Table 1, and include: DNA topoisomerase (Liu, *Ann. Rev. Biochem.* 58, 351–375 1989), lamin B (Lazebnik et al., *Proc. Natl. Acad. Sci. USA* 92, 9042–9046. 1995), NuMA (Compton, 1994), PARP (Lazebnik et al., Supra, 1994), and Ul-70kDa (Casciola-Rosen et al., *J. Biol. Chem.* 49, 30757–30760. 1994). and the like.

As used herein, "ability to modulate apoptotic activity of TRAIL receptors" refers to a compound that has the ability to either induce (agonist) or inhibit (antagonist) apoptosis mediated by DR5 or TRAIL-R3 proteins.

In another embodiment of the present invention, the bioassay for evaluating whether test compounds are capable of acting as antagonists for DR5 and TRAIL-R3 proteins of the invention, or functional modified forms of said DR5 and TRAIL-R3 proteins, comprises:

(a) culturing cells containing: DNA which expresses DR5 and TRAIL-R3 proteins, or functional modified forms thereof, wherein said culturing is carried out in the presence of: increasing concentrations of at least one compound whose ability to inhibit apoptotic activity of DR5 and TRAIL-R3 proteins is sought to be determined, and a fixed concentration of TRAIL; and thereafter (b) monitoring in said cells the level of apoptosis as a function of the concentration of said compound, thereby indicating the ability of said compound to inhibit DR5 or TRAIL-R3 mediated apoptotic activity.

In step (a) of the above-described antagonist bioassay, culturing may also be carried out in the presence of:

fixed concentrations of at least one compound whose ability to inhibit apoptotic activity of DR5 and TRAIL-R3 proteins is sought to be determined, and an increasing concentration of TRAIL.

Host cells contemplated for use in the bioassay(s) of the present invention include MCH6 cells, 293 cells, CV-1 cells, COS cells, HeLa cells, and the like. Presently, preferred host cells for carrying invention bioassays are HeLa cells as described in Example VI.

Also contemplated in yet another embodiment of the present invention, is a method for modulating the apoptotic activity mediated by DR5 or TRAIL-R3 proteins, said method comprising:

contacting an DR5 or TRAIL-R3 protein with an effective, modulating amount of an agonist or antagonist identified by the above-described bioassays.

The present invention also contemplates therapeutic compositions useful for practicing the therapeutic methods described herein. For example, the above described DR5 or TRAIL-R3 polypeptides can also be formulated into pharmaceutical compositions known within the art for the treatment of programmed cell death mediated diseases characterized by increased or decreased cell survival and proliferation. Functional fragments and peptides such as the extracellular TRAIL-binding domains and the cytoplasmic death domain of DR5 or TRAIL-R3 can similarly be formulated for the treatment of such diseases associated with increased or decreased cell survival and proliferation. Additionally, molecules that interact with DR5 or TRAIL-R3 can additionally be used to modulate DR5 or TRAIL-R3 mediated apoptosis. Administration of DR5 polypeptides and functional fragments thereof may induce or inhibit apoptosis in treated cells, and may eliminate those cells characterized by increased cell survival or proliferation.

Treatment or reduction of the severity of cell death mediated diseases can also be accomplished by introducing expressible nucleic acids encoding DR5 or TRAIL-R3 polypeptides or functional fragments thereof into cells characterized by such diseases. Elevated synthetic rates of DR5 or TRAIL-R3 may be achieved, for example, by using recombinant expression vectors and gene transfer technology. Similarly, treatment or reduction of the severity of cell death mediated diseases may also be accomplished by introducing and expressing antisense DR5 or TRAIL-R3 nucleic acids so as to inhibit the synthesis rates of DR5 or TRAIL-R3. Such methods are well known within the art and are described herein with reference to recombinant viral vectors. Other vectors compatible with the appropriate targeted cell can accomplish the same goal and therefore can be substituted in the methods described herein in place of recombinant viral vectors.

Therapeutic compositions of the present invention contain a physiologically compatible carrier together with DR5 or TRAIL-R3 polypeptides or functional fragments thereof, a DR5 or TRAIL-R3 modulating agent, or an anti-DR5 or anti-TRAIL-R3 antibody, as described herein, dissolved or dispersed therein as an active ingredient.

As used herein, the terms "pharmaceutically acceptable", "physiologically acceptable" and grammatical variations thereof, as they refer to compositions, carriers, diluents and reagents, are used interchangeably and represent that the materials are capable of administration to a mammal without the production of undesirable physiological effects such as nausea, dizziness, gastric upset, and the like.

The preparation of a pharmacological composition that contains active ingredients dissolved or dispersed therein is well known in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients that are pharmaceutically acceptable and compatible with the active ingredient in amounts suitable for use in the therapeutic methods described herein. Suitable excipients are, for example, water, saline, dextrose, glycerol, ethanol, or the like, as well as combinations of any two or more thereof. In addition, if desired, the composition can contain minor amounts of auxiliary substances such as wetting or emulsifying agents, pH buffering agents, and the like, which enhance the effectiveness of the active ingredient.

The therapeutic composition of the present invention can include pharmaceutically acceptable salts of the components therein. Pharmaceutically acceptable nontoxic salts include the acid addition salts (formed with the free amino groups of the polypeptide) that are formed with inorganic acids such as, for example, hydrochloric acid, hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Salts formed with the free carboxyl groups can also be derived from inorganic bases such as, for example, sodium hydroxide, ammonium hydroxide, potassium hydroxide, and the like; and organic bases such as mono-, di-, and tri-alkyl and -aryl amines (e.g., triethylamine, diisopropyl amine, methyl amine, dimethyl amine, and the like) and optionally substituted ethanolamines (e.g., ethanolamine, diethanolamine, and the like).

Physiologically tolerable carriers are well known in the art. Exemplary liquid carriers are sterile aqueous solutions that contain no materials in addition to the active ingredients and water, or contain a buffer such as sodium phosphate at physiological pH, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary additional liquid phases include glycerin, vegetable oils such as cottonseed oil, and water-oil emulsions.

As described herein, an "effective amount" is a predetermined amount calculated to achieve the desired therapeutic effect, e.g., to modulate the TRAIL mediated apoptotic activity of an invention DR5 or TRAIL-R3 protein. The required dosage will vary with the particular treatment and with the duration of desired treatment. Such dosages are known or can be easily determined by those skilled in the art. Administration may be accomplished, for example, by intravenous, interperitonal or subcutaneous injection. Administration may be performed in a variety of different regimes, which include single high dose administration or repeated small dose administration, or a combination of both. The dosing may depend on the cell type, progression of the disease and overall health of the individual, and will be known or can be determined by those skilled in the art.

It is contemplated that dosages between about 10 micrograms and about 1 milligram per kilogram of body weight per day may be used for therapeutic treatment. It may be particularly advantageous to administer such compounds in depot or long-lasting form as discussed herein. A therapeutically effective amount is typically an amount of an DR5- or TRAIL-R3-modulating agent or compound identified herein that, when administered in a physiologically acceptable composition, is sufficient to achieve a plasma concentration of from about 0.1 $\mu$g/ml to about 100 $\mu$g/ml, preferably from about 1.0 $\mu$g/ml to about 50 $\mu$g/ml, more preferably at least about 2 $\mu$g/ml and usually 5 to 10 $\mu$g/ml.

All U.S. patents and all publications mentioned herein are incorporated in their entirety by reference thereto. The invention will now be described in greater detail by reference to the following non-limiting examples.

EXAMPLES

Unless otherwise stated, the present invention was performed using standard procedures, as described, for example in Maniatis et al., *Molecular Cloning: A Laboratory Manual,* Cold Spring Harbor Laboratory Press, Cold Spring Harbor, N.Y., USA (1982); Sambrook et al., *Molecular Cloning: A Laboratory Manual* (2 ed.), Cold Spring Harbor Laboratory Press, Cold Spring Harbor, New York, USA (1989); Davis et al., *Basic Methods in Molecular Biology,* Elsevier Science Publishing, Inc., New York, USA (1986); or *Methods in Enzymology: Guide to Molecular Cloning Techniques* Vol 152, S. L. Berger and A. R. Kimmerl Eds., Academic Press Inc., San Diego, USA (1987).

EXAMPLE I

Cloning and Characterization of DR5 and TRAIL-R3

This example demonstrates the identification and cloning of DR5 and TRAIL-R3 cDNA. Briefly, several EST clones were identified and their 3' and 5' sequences were compiled. Based on the compiled sequences, PCR primers were generated and used to clone two cDNAs which encode two novel members of the TRAIL-receptor family (FIGS. 1A and 1B).

To identify novel members of the TNF-receptor family, an approach combining information from the GenBank database of human expressed sequence tags (ESTs) and PCR was employed (see Alnemri E. S. et al. (1996) *Proc. Natl. Sci. USA.* 93, 7464–7469; Fernandez-Alnemri et al., *Cancer Res.* 5S:2737–2742 (1995); and Fernandez-Alnemri et al., *Cancer Res.* 55:6045–6052 (1995)). Initially, a search of the GenBank EST data base for sequences related to TRAIL receptor-1, also referred to as "DR4", identified several EST clones, which were used to derive 5' and 3' PCR primers to clone related cDNAs.

The EST sequences used to clone DR5 were identified as human GenBank EST clone 650744 (Accession Nos. AA223122 and AA223238) and clone 664665 (Accession Nos. AA232424 and AA232440). These EST clones were used to design primers at the extreme 5' and 3' ends of the DR5 coding region. The 5' primer employed to amplify DR5 cDNA corresponded to the oligonucleotide set forth as nucleotides 1–18 of SEQ ID NO:1. The 3' primer used corresponds to the oligonucleotide complementary to nucleotides 1219–1236 of SEQ ID NO:1.

Similarly, the EST sequences used to clone TRAIL-R3 were identified as human GenBank EST clone 470799 (Accession No. AA031883), clone 129137 (Accession Nos. R10995 and R10996) and clone 504745 (Accession Nos. AA150849 and AA150541). These EST clones were used to design primers at the extreme 5' and 3' ends of the TRAIL-R3 coding region. The 5' primer employed to amplify TRAIL-R3 cDNA co-responded to the oligonucleotide set forth as nucleotides 1–18 of SEQ ID NO:3. The 3' primer used corresponds to the oligonucleotide complementary to nucleotides 883–900 SEQ ID NO:3.NO:1.

A 10 $\mu$l aliquot of human Jurkat $\lambda$ Uni-Zap™ XR cDNA library (Femandez-Alnemri et al., *J. Biol. Chem.* 269:30761–30764 (1994)) containing approximately 108 pfu was denatured at 99° C. for 5 min. and used as a template for PCR amplification with the above-described primer pairs for cloning DR5 and TRAIL-R3 cDNA. The full-length amplification products were cloned into a small-cut pBluescript II KS⁺ vector and sequenced.

To confirm the sequence of the PCR-amplified DR5 and TRAIL-R3 cDNA, the cloned cDNA was then excised from the vector, radiolabeled and used to screen the original Jurkat k Uni-ZapTM XR cDNA library for full length cDNA clones. Positive A plones were purified, rescued into the pBluescript II SK⁻ plasmid vector and sequenced for confirmation.

FIGS. 1A–1D show the sequence analysis and tissue distribution of invention DR5 and TRAIL-R3 proteins. The predicted amino acid sequence of human DR5 and TRAIL-R3 is set forth in FIGS. 1A and 1B, respectively. The mature DR5 and TRAIL-R3 proteins start at Glu+1 and Tyr+1 (indicated by black diamonds), respectively. The signal peptide and transmembrane domains are single- and double-underlined, respectively. The five identical repeats in the extracellular domain of TRAIL-R3 (FIG. 1B) are marked by black triangles. The intracellular cytoplasmic death domain of DR5 (FIG. 1A) is boxed.

The DR5 cDNA encodes a protein of 411 amino acids (SEQ ID NO:2) with an overall ~59% amino acid identity to DR4 (FIG. 1A). Its domain structure is highly related to DR4 and the other members of the TNF-receptor family. DR5 contains a putative N-terminal signal peptide (amino acids −51 to −1 of FIG. 1A) followed by an extracellular domain containing two cysteine-rich pseudorepeats. Following the extracellular domain is a transmembrane domain (amino acids 132–152 of FIG. 1A) and a cytoplasmic domain. Within the cytoplasmic domain there is a stretch of 67-amino acids (amino acids 273–339 of FIG. 1A) comprising a death domain homology region (FIG. 1C). Based on these criteria and its apoptotic activity (see Example IV below) this TRAIL-receptor protein was designated death receptor-5 (DR5) (also referred to herein as TRAIL-R2).

The TRAIL-R3 cDNA encodes a protein of 299 amino acids with an overall ~40% and 36% amino acid identity to DR4 and DR5, respectively (FIG. 1B). TRAIL-R3 contains an N-terminal signal peptide (amino acids −63 to −1 of FIG. 1B) followed by an extracellular domain containing two cysteine-rich pseudorepeats and five nearly identical PAAEETMN(T)TSPGTPA repeats (amino acids 139–153, 154–168, 169–183, 184–198, and 199–213 of FIG. 1B). Following the extracellular domain is a C-terminal transmembrane domain (amino acids 217–236 of FIG. 1B). Unlike DR4 and DR5, TRAIL-R3 does not contain a cytoplasmic domain. Based on these criteria and its ability to bind TRAIL (see Example III below), this protein was designated TRAIL-R3.

FIG. 1C shows a colinear alignment of the death domains of members of the TNF receptor family. Identical residues in at least three out of six sequences are shaded. The death domain of DR5 is 64, 30, 30, 20, 31% identical to the corresponding domains in DR4, DR3, TNFR-1, Fas and CAR1, respectively.

EXAMPLE II

Expression Analyst. of DR5 and TRAIL-R3 mRNA

This example demonstrates the mRNA expression patterns of DR5 and TRAIL-R3 in normal and tumor cells.

FIG. 1D shows a Northern blot analysis of the expression of DR5 (upper panels) and TRAIL-R3 (lower panels) mRNAs in normal tissues and tumor cell lines. X-ray film exposure time in the two lower panels and the upper left panel was for 48 hours, whereas in the upper right panel was for 2 hours. The cell lines assayed were: HL-60, promyelocytic leukemia; HeLa cell S3, K-562, chronic myelogenous leukemia; MOLT-4, lymphoblastic leukemia; Raji, Burkitt's lymphoma; SW480, colorectal adenocarcinoma; A549, lung carcinoma; G361, melanoma. Numbers on the right in FIG. 1D indicate kilobases.

Northern blot analysis of equivalent amounts of mRNA samples from normal human tissues and tumor cell lines, with a DR5 riboprobe, detected a ~4 kb transcript in all the samples (FIG. 1D, upper panels). Surprisingly, the amount of DR5 transcript was at least a 100-fold more in most tumor cell lines than in normal tissues. Autoradiography for less than 2 h was sufficient to detect the DR5 message in tumor cell lines, compared to 48 h in the case of the normal tissues. Other abnormal tissues such testes, ovary, colon, small intestine and lymphoid tissues had detectable but low expression of DR5 transcript, similar to that observed in the normal tissues shown in FIG. 1D.

The TRAIL-R3 riboprobe detected 5 kb message in both normal human tissues and tumor cell lines (FIG. 1D, lower panels). A significantly elevated expression of TRAIL-R3 mRNA in normal compared to tumor cells was observed. Given the activities of these two receptors (see below), this could explain the high sensitivity of tumor cell lines to TRAIL compared to normal cells (Davis T. D. et al. (1995) *Immunity* 3, 673–682; Ashkenazi A. et al. (1996) *J. Bio. Chem.* 271, 12687–12690; Ashkenazi A. et al. (1996) *Curr. Biol.* 6, 750–752).

EXAMPLE III

Trail Binding Assay

This example demonstrates that DR5 and TRAIL-R3 are receptors for the cytotoxic ligand TRAIL and can block TRAIL-induced apoptosis.

To generate C-terminal Fc-tagged receptors, PCR generated cDNAs encoding Fas (residues −16-158), DR4 (residues 86-217, with N-terminal Fas signal peptide-Flag tag), DR5 (residues −51-133) and TRAIL-R3 (residues −63-217) extracellular domains were inserted into a modified pcDNA3 vector that allowed for inframe fusion with the Fc portion of the mouse IgG.

Recombinant soluble TRAIL with N-terminal T7 and His6 tags was obtained by Ni-affinity purification from bacteria transformed with a pET28c-TRAIL (residues 95-281) vector. Receptor-Fc chimeras were obtained by harvesting conditioned media of 293 cells transfected with constructs encoding Fas-, DR4-, DR5- or TRAIL-R3-Fc fusion proteins as described (Chinnaiyan, A. M. et al. (1997) *Science* 276, 111–113). Binding of TRAIL to the receptor-Fc chimeras was performed as described (Chinnaiyan, A. M. et al. (1997) *Science* 276, 111–113).

Figure 2A:
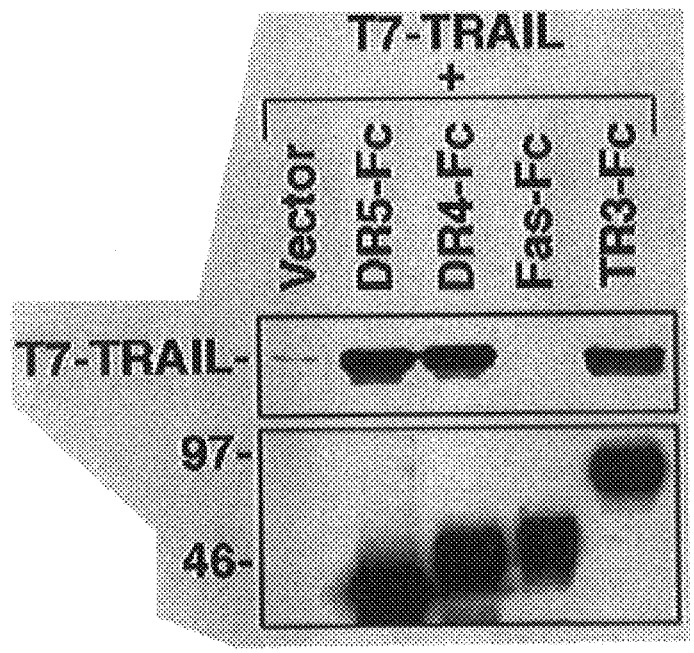

FIG. 2 shows that the extracellular domains of DR5 and TRAIL-R3 bind TRAIL and can block TRAIL-induced apoptosis. FIG. 2A shows the results of an assay in which conditioned media from cultures of 293 cells transfected for 72 h with empty vector (lane 1), or DR5 (lane 2), DR4 (lane 3), Fas (lane 4) or TRAIL-R3 (TR3-Fc) (lane 5) extracellular domain-Fc fusion proteins, were incubated with purified soluble T7-His6-TRAIL and then immunoprecipitated with anti-mouse IgG-agarose. After extensive washing the samples were analyzed by SDS-PAGE and immunoblotted with a horseradish peroxidase (HRP) -conjugated T7-antibody (upper panel). The corresponding receptor-Fc fusions in the conditioned media were also immunoblotted with anti-mouse Fc antibody (lower panel).

FIG. 2B shows the results of an assay in which aliquots of conditioned media containing receptor-Fc fusion proteins or no fusion protein (vector) were incubated with equivalent amount of soluble TRAIL (250 ng/ml) and then added to MCF7 cells. Cells were stained 8 hours later with propidium iodide and the nuclei were examined by fluorescence microscopy. The graph shows the percentage of apoptotic nuclei (mean±SD) as a function of total nuclei counted under each condition (n=3).

As set forth above, the extracellular-ligand binding domains of Fas, DR4, DR5 and TRAIL-R3 were expressed as fusion proteins with the Fc region of mouse IgG (FIG. 2A, lower panel). As shown in FIG. 2A, upper panel, DR4-Fc, DR5-Fc and TRAIL-R3-Fc were all capable of binding TRAIL to the same extent (lanes 2, 3 and 5). As expected Fas-Fc was unable to bind TRAIL (lane 4). Furthermore, DR4-Fc, DR5-Fc and TRAIL-R3-FC, but not Fas-Fc, were capable of blocking TRAIL-induced apoptosis in MCF7 cells (FIG. 2B). These data indicate that, like DR4, DR5 and TRAIL-R3 are receptors for TRAIL.

EXAMPLE IV

Apoptotic Activity of DR5 and TRAIL-R3

This example demonstrates that DR5 but not TRAIL-R3 induces apoptosis in human cells.

For apoptosis assays the mammalian double expression vector pRSC (Akporiaye E. T. et al. (1997) *BioTech.* 22, 68) was used, which allows for expression of lacZ under the RSV promoter and the test cDNA (DR4, DR4A, DR5, DR5A, TRAIL-R3) under the CMV promoter. CrmA, FLAME-1, caspase-8-DN (C345A) or caspase-10-DN (C358A) (Alnemnri E. S. et al. (1997) *J. Biol. Chem.* 272, 18542-18545) were expressed using pcDNA3 (Invitrogen).

FIG. 3 illustrates that expression of DR5 but not TRAIL-R3 induces apoptosis in human cells. MCF7 (FIG. 3A) and 293 (FIG. 3B) cells were transfected with the indicated pRSC-lacZ constructs. Thirty hours after transfection cells were stained with Pgal and examined for morphological signs of apoptosis. The graphs show the percentage of round blue apoptotic cells (mean +SD) as a function of total blue cells under each condition ($\geq 23$).

FIG. 3C shows that ectopic expression of TRAIL-R3 attenuates TRAIL-induced apoptosis in MCF7 cells. MCF7 cells were transfected with TRAIL-R3 or vector alone for 36 h, then treated with soluble TRAIL (250 ng/ml) for 8 h. The data are represented as in FIGS. 3A and 3B, after subtracting the background killing (12–15%) as a result of transfection.

FIGS. 3D and 3E show that DR4-induced and DR5-induced apoptosis is inhibited by the caspase inhibitors, z-VAD-fmk and CrmA (FIG. 3D), and by the dominant negative inhibitors, caspase-8-DN, caspase-10-DN and FLAME-1 (FIG. 3E). MCF7 cells were transfected with DR4 or DR5 expression constructs in the presence of z-VAD-fmk (20 $\mu$M) or co-transfected with a four-fold excess of a CrmA, caspase-8-DN, caspase-10-DN or FLAME-1 construct or an empty vector. The data are represented as in FIGS. 3A and 3B.

It is known that ectopic expression of death domain-containing members of the TNF-receptor family induces apoptosis in a ligand-independent manner. Consistent with this observation, it has been found that transient expression of DR5 in MCF7 cells or 293 cells triggers apoptosis (FIGS. 3A and 3B). The level of apoptosis induction was similar to that observed with DR4 (FIG. 3A). DR5 induction of apoptosis was dependent on the presence of the cytoplasmic death domain, as deletion of this domain abolished the ability of DR4 and DR5 to induce apoptosis (FIGS. 3A and 3B). In contrast, TRAIL-R3 which does not naturally contain a death domain was incapable of inducing apoptosis (FIGS. 3A and 3B). Interestingly, transient expression of TRAIL-R3 in MCF7 cells significantly blocked TRAIL-induced apoptosis (FIG. 3C), suggesting that TRAIL-R3 functions as an antagonistic decoy receptor.

Similar to DR4 and other TNF-receptor family members, DR5-induced apoptosis was efficiently blocked by the caspase inhibitors z-VAD-fmk and CrmA (FIG. 3D). DR4-induced and DR5-induced apoptosis was also significantly inhibited by the dominant negative inhibitors FLAME-1 (also known as Casper, FLIP, I-FLICE, CASH) (Alnemri E. S. et al. (1997) *J. Biol. Chem.* 272, 18542–18545; Wallach, D. (1997) Nature 388, 123–125; and references therein), caspase-8-DN and caspase-10-DN (FIG. 3E). Among these, caspase-10-DN was the most effective in blocking DR4-included and DR5-induced apoptosis. Inhibition of DR4-induced and DR5-induced apoptosis by FLAME-1 is consistent with recent observations that TRAIL-induced apoptosis is blocked by expression of FLIP (FLAME-1) (Bodmer J. L. et al. (1997) *Nature* 388, 190–195). These data also suggest that the upstream caspases-8 and -10 are involved in both the DR4 and DR5 death signaling pathways.

EXAMPLE V

In Vivo Interactions of DR5

This example demonstrates that DR4 and DR5 recruit caspase-8, caspase-10 and FLAME-1 to the death signaling pathway.

T7-epitope tagging was done as described recently (Alnemri E. S. et al. (1997) J. Biol. Chem. 272, 18542–18545. To generate N-terminal Flag-tagged receptor and receptor mutants, PCR generated cDNAs encoding Fas, DR4, DR4A (residues 86-351), DR5, DR56 (residues 1-268) were inserted in a modified pcDNA-3 vector that allowed for inframe fusion with a Flag-epitope tag that is preceded by Fas-signal peptide.

Death domain containing adaptor molecules such as FADD/MORT1, CRADD/RAIDD, TRADD and RIP are recruited by some members of the TNF-receptor family to engage the upstream caspases (Nagata, S. (1997) Cell 88, 355–365); Alnemri E. S. et al. (1997) *J. Biol. Chem.* 272, 18542–18545). Using co-immunoprecipitation experiments, DR5 was assayed to determine whether it could interact with these molecules to transmit the apoptotic signal.

Figure 4A:
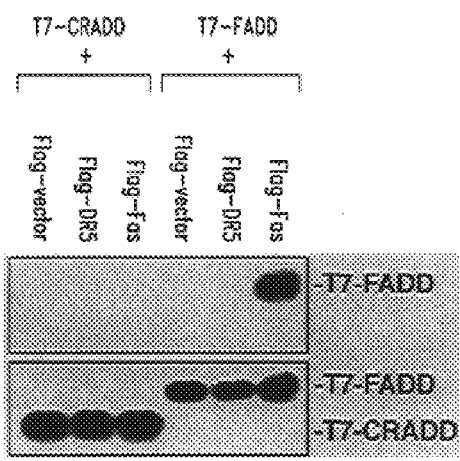
FIGS. 4A and 4B illustrate the in vivo interactions of DR5 as set forth in Example V herein.

FIG. 4 illustrates the in vivo interactions of DR5. FIG. 4A shows that DR5 does not recruit FADD or CRADD. 293 cells were transfected with expression plasmids encoding T7-epitope tagged CRADD or FADD and Flag-epitope tagged Fas or DR5. After 36 h, extracts were prepared and immunoprecipitated with a monoclonal antibody to the Flag-epitope. The immunoprecipitates (upper panel) and the corresponding cellular extracts (lower panel) were analyzed by SDS-PAGE and immunoblotted with a HRP-conjugated T7-antibody.

Figure 4B:
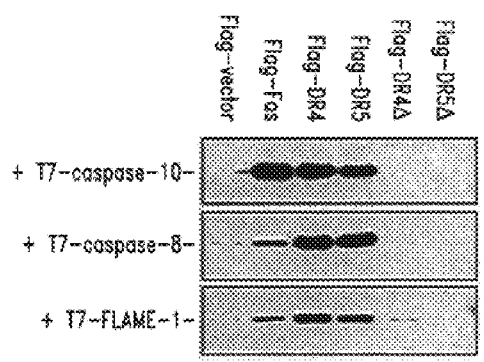

FIG. 4B shows that caspase-8, caspase-10 and FLAME-1 are recruited to the Fas, DR4 and DR5 signaling complexes. Briefly, 293 cells were co-transfected with the indicated Flag constructs and plasmids encoding T7-caspase-10 (upper panel), T7-caspase-8 (middle panel) or T7-FLAME-1 (lower panel) and then immunoprecipitated and detected as in FIG. 4A.

Unlike Fas, DR5 did not interact with FADD or CRADD (FIG. 4A), nor with RIP or TRADD. A similar observation was reported with DR4 (Pan et al., 1997, Science 276, 111–113). Interestingly, full length Fas, DR4 and DR5, but not death domain-deleted mutants, were all capable of forming complexes with caspase-8, caspase-10 and FLAME-1 (FIG. 4B). Since these proteins do not interact directly, it is believed that formation of these complexes would require an adaptor molecule distinct from FADD.

Although the invention has been described with reference to the examples provided above, it should be understood that various modifications can be made without departing from the spirit of the invention. Accordingly, the invention is limited only by the claims.

What is claimed is:

1. An isolated polypeptide comprising SEQ ID NO:6.
2. A fragment of a DR5 splice variant polypeptide said fragment comprising amino acids 183 to 211 of SEQ ID NO:6.

* * * * *